(12) United States Patent
Drewett et al.

(10) Patent No.: US 11,480,557 B2
(45) Date of Patent: Oct. 25, 2022

(54) SENSING APPARATUS FOR USE WITH A CONCRETE STRUCTURE

(71) Applicant: Senceive Ltd, Milton Keynes (GB)

(72) Inventors: Thomas Drewett, London (GB); Bryn Anthony Smith, London (GB)

(73) Assignee: SENCEIVE LTD, Milton Keynes (GB)

( * ) Notice: Subject to any disclaimer, the term of this patent is extended or adjusted under 35 U.S.C. 154(b) by 40 days.

(21) Appl. No.: 16/768,498

(22) PCT Filed: Nov. 29, 2018

(86) PCT No.: PCT/GB2018/053465
§ 371 (c)(1),
(2) Date: May 29, 2020

(87) PCT Pub. No.: WO2019/106376
PCT Pub. Date: Jun. 6, 2019

(65) Prior Publication Data
US 2020/0300832 A1 Sep. 24, 2020

(30) Foreign Application Priority Data

Nov. 30, 2017 (GB) ...................................... 1719917

(51) Int. Cl.
*G01N 33/00* (2006.01)
*G01N 33/38* (2006.01)
(Continued)

(52) U.S. Cl.
CPC ............. *G01N 33/383* (2013.01); *G01C 9/02* (2013.01); *G01L 1/2287* (2013.01); *G01P 1/00* (2013.01); *G01P 15/02* (2013.01); *H04W 84/18* (2013.01)

(58) Field of Classification Search
CPC ...... G01N 33/383; G01C 9/02; G01L 1/2287; G01P 1/00; G01P 15/02; H04W 84/18
See application file for complete search history.

(56) References Cited

U.S. PATENT DOCUMENTS

| 2009/0202296 A1* | 8/2009 | Lamore | .................. E01F 13/06 404/6 |
| 2016/0148501 A1* | 5/2016 | Mou | ........................ H04Q 9/00 340/870.02 |
| 2017/0252256 A1* | 9/2017 | Henshue | .............. G09B 21/004 |

FOREIGN PATENT DOCUMENTS

| FR | 3033586 A1 | 9/2016 |
| WO | 0246701 A1 | 6/2002 |
| WO | WO-2019106376 A1 * | 6/2019 ............. G01P 15/02 |

OTHER PUBLICATIONS

International Preliminary Report on Patentability for International Application No. PCT/GB2018/053465, entitled, "A Sensing Apparatus for Use with a Concrete Structure," dated Jun. 2, 2020.
(Continued)

*Primary Examiner* — Max H Noori
(74) *Attorney, Agent, or Firm* — Hamilton, Brook, Smith & Reynolds, P.C.

(57) ABSTRACT

A battery-powered sensing apparatus adapted for embedding in concrete comprises a housing having a base portion and a removable lid, the housing providing a sealed enclosure, and at least one sensor for monitoring one or more environmental conditions for the concrete. The sensing apparatus further comprises a control module; a wireless communication module; and a battery. The control module, wireless communication module and battery are mounted on the lid so as to be located within the sealed enclosure as internal components, and so as to be removable with the lid after the sensing apparatus has been embedded in concrete.

19 Claims, 9 Drawing Sheets

(51) Int. Cl.
*G01C 9/02* (2006.01)
*G01L 1/22* (2006.01)
*G01P 1/00* (2006.01)
*G01P 15/02* (2013.01)
*H04W 84/18* (2009.01)

(56) References Cited

OTHER PUBLICATIONS

International Search Report and Written Opinion for International Application No. PCT/GB2018/053465, entitled, "A Sensing Apparatus for Use with a Concrete Structure," dated Feb. 13, 2019.
Search Report Under Section 17(5) for GB Application No. GB1719917.5, entitled, "A Sensing Apparatus for Use with a Concrete Structure," dated Apr. 19, 2018.

* cited by examiner

SENSING APPARATUS FOR USE WITH A CONCRETE STRUCTURE

This application is the U.S. National Stage of International Application No. PCT/GB2018/053465, filed Nov. 29, 2018, which designates the U.S., published in English, and claims priority under 35 U.S.C. § 119 or 365(c) to Great Britain Application No. 1719917.5, filed Nov. 30, 2017. The entire teachings of the above applications are incorporated herein by reference.

FIELD

The present invention relates to a sensing apparatus for use with a concrete structure, for example, for embedding within such a concrete structure.

BACKGROUND

The construction industry uses a variety of instrumentation to perform monitoring of structures such as tunnels, bridges, buildings and so on. Such instrumentation typically comprises sensors that are rigidly attached, for example by screws, to a structure to be monitored. In many situations, the monitoring is performed at locations that do not have a pre-existing or at least a readily accessible wired infrastructure for providing power and/or for supporting data communications to/from the sensors. In these circumstances, it is attractive for the sensors to use wireless communications and to be battery-powered devices. Examples of such sensors and their use by Senceive Ltd (see www.senceive.com) are described, inter alia, in PCT/GB2014/050245 and in GB1408400.8, the contents of which are incorporated herein by reference.

In certain environments it is desirable for a sensor apparatus to be embedded in a concrete structure. For example, in an underground rail system (or more generally in a tunnel for trains or other vehicles), it may be undesirable for the sensor apparatus to protrude into the tunnel itself, thereby to avoid possible damage to the sensor apparatus by vehicle traffic passing through the tunnel (and conversely also any possible damage to the vehicle traffic by the sensor apparatus). The confined spaces of such environments may also hinder maintenance operations, in that it may not be feasible to perform such maintenance operations while the tunnel is in operational use—e.g. in view of safety or other practical considerations. However, closing a tunnel to normal operational use may be expensive and highly disruptive.

SUMMARY

The invention is defined in the appended claims.

One aspect described herein is a battery-powered sensing apparatus adapted for embedding in concrete. The sensing apparatus comprises an enclosure or housing having a base portion and a removable lid, the housing providing a sealed cavity. The sensing apparatus further comprises at least one sensor for monitoring one or more environmental conditions for the concrete; a control module; a wireless communication module; and a battery. The control module, wireless communication module and battery are mounted on the lid so as to be located within the sealed enclosure as internal components, and so as to be removable with the lid after the sensing apparatus has been embedded in the concrete.

Mounting the internal components on the lid enables efficient removal of the internal components from the sensing apparatus, for example for maintenance, such as battery replacement, or upgrade, whereby a new lid with a new set of internal components might be installed. Such maintenance and upgrade facilities support an overall operational lifetime for the sensing apparatus which is comparable with that of the concrete itself—typically many decades. Furthermore, the above approach allows the installation of the internal components to be delayed (if so desired) until the concrete has been installed on-site, thereby avoiding the risk that such components might be damaged during casting, transportation or installation of the concrete.

In some cases the sensing apparatus includes a sensor, such as a tilt sensor, located internally within the sealed enclosure, the sensor being mounted on the lid like the other internal components as described above to support easier maintenance, etc. In some cases, the sensing apparatus additionally (or alternatively) includes a sensor, such as a strain gauge (e.g. a vibrating wire strain gauge), to be located externally to the sealed enclosure, embedded within the concrete. The sensing apparatus further comprises a wired link from the externally located sensor into the sealed enclosure, and a terminal module, such as a passive printed circuit board, located in the base portion of the housing. The terminal module may be a dumb connector in that it does not include any active components. The terminal module provides an interface between (i) the wired link from the externally located sensor and (ii) wiring from the internal components within the sealed enclosure; the latter may be provided with a plug to allow easy fitting into, and removal from, the terminal module. The terminal module may be for example a connector such as a printed circuit board with connectors for the embedded sensors and an umbilical connector to the control module and the wireless communications modules on the lid.

Since the external sensor is embedded within the concrete, it cannot be accessed (other than electrically via the wired connection). The terminal module or connector can potentially be accessed within the sensing apparatus, but is generally intended to remain within the sensing apparatus without further maintenance or upgrade for the lifetime of the device, this being supported by the terminal module (connector) having no additional functionality beyond providing the desired electrical connectivity (i.e. a connector). The plug fitting between the terminal module and wiring from the internal components supports straightforward disconnection and (re)connection if the latter are removed (with the lid) during maintenance operation. It will be appreciated that the sensing apparatus may have one or more internal sensors and/or one or more external sensors.

The use of a battery for powering the sensing apparatus and wireless communications for transmitting sensed data avoids having to provide external wiring to the sensing apparatus. In some implementations, the wireless communication module is adapted to form a node in a wireless mesh network. The wireless communication module may support self-configuration of the wireless mesh network, and is also able to go into a low-power mode between pre-scheduled communication sessions with other nodes in the wireless mesh network. For example, the wireless communication module may communicate with other nodes in the wireless network according to a time-synchronised schedule, such that transmit and receive circuits of the wireless communication system are in operation with an average duty cycle of less than 5%, preferably less than 1%. The synchronisation between nodes of the wireless communication network improves energy efficiency, and so helps to extend the operational battery lifetime. In other examples the wireless communications module may communicate with other nodes in a geographical wide area network (geowan) using non-synchronous communications.

The sensing apparatus described above can be combined with (mounted on) a structure for embedding within the concrete to provide reinforcement of the concrete; for example, such a structure may comprise reinforcing bars (rebars), or a grill or grating. This reinforcing structure provides effective anchoring of the sensing apparatus within the concrete, but at the same time has minimal disruption to the overall design, manufacture and installation of the concrete.

A sensing apparatus as described herein may be embedded in a concrete slab which may be for example curved to form part of a tunnel lining. In other examples the sensing apparatus may be embedded into a precast railway slab track or a slab of other configuration. The sensing apparatus may be embedded into a pre-cast slab or element or may be cast in situ. In some examples the sensing apparatus may be formed into a railway sleeper of similar structure supporting railway tracks. In this case, the lid of the sensing apparatus is located on the intrados surface of the concrete slab and may be substantially flush with the surface of the concrete slab (so as to maximise clearance for vehicles passing through the tunnel).

In one example the enclosure of the sensing apparatus may be formed with side-walls for attachment to the base portion. In another example, a casting negative may be used for temporary attachment to the base portion so that after the concrete has been cast and the casting negative removed, side-walls of the enclosure are formed from the concrete of the slab, the casting negative forming a void in which components of the sensing apparatus can be located.

Another aspect described herein is a battery-powered sensing apparatus adapted for embedding in concrete. The sensing apparatus comprises a housing having a base portion and a removable lid, the housing providing a sealed enclosure. The sensing apparatus further comprises at least one sensor for monitoring one or more environmental conditions for the concrete; a control module; a wireless communication module; and a battery. The sensing apparatus is adapted to have an operation substantial lifetime such as for example a lifetime of at least 10 years after the sensing apparatus has been embedded in the concrete.

Such an operational lifetime may be supported, inter alia, by the battery having a substantial charge capacity such as for example a charge capacity of at least 10 Ampere hours; the control module comprising a microcontroller having a sleep mode drawing less than 0.01 milliamps; and the wireless communication module having a duty cycle of less than 5% and drawing less than 0.01 miliamps when the duty cycle is off—i.e. when there is no active signal transmission or reception. (Other features of this sensing apparatus may be the same as for the sensing apparatus described above).

Another aspect described herein is a method for forming a precast concrete segment with an embedded sensing apparatus. The concrete segment could be for example a curved tunnel, a slab track, a cut-and-cover tunnel, a wall or other structural component. The method comprises constructing a sub-unit comprising a sealed enclosure and a reinforcing structure; attaching the sub-unit to a casting mould via the reinforcing structure; and casting the concrete into the mould to embed the sub-unit. According to the present technique, the components of the sensing apparatus are secured within sealed enclosure forming part of a concrete component of a structure to be monitored such as for example a railway tunnel.

A sensing apparatus as described herein may be used, for example, to measure an environmental condition such as distortion or movement of the concrete structure in which the sensor assembly is embedded. Typically multiple sensor assemblies (a network of such assemblies) are embedded within the structure to provide a more accurate determination of any movement or distortion across a larger region of the structure. Examples of such concrete structures are tunnels (for the underground/subway, for ordinary rail or road traffic, etc), buildings, bridges, rail networks, dams, embankments, and so on.

BRIEF DESCRIPTION OF THE DRAWINGS

Various embodiments of the invention will now be described in detail by way of example only with reference to the following drawings.

DETAILED DESCRIPTION

Figure 1:
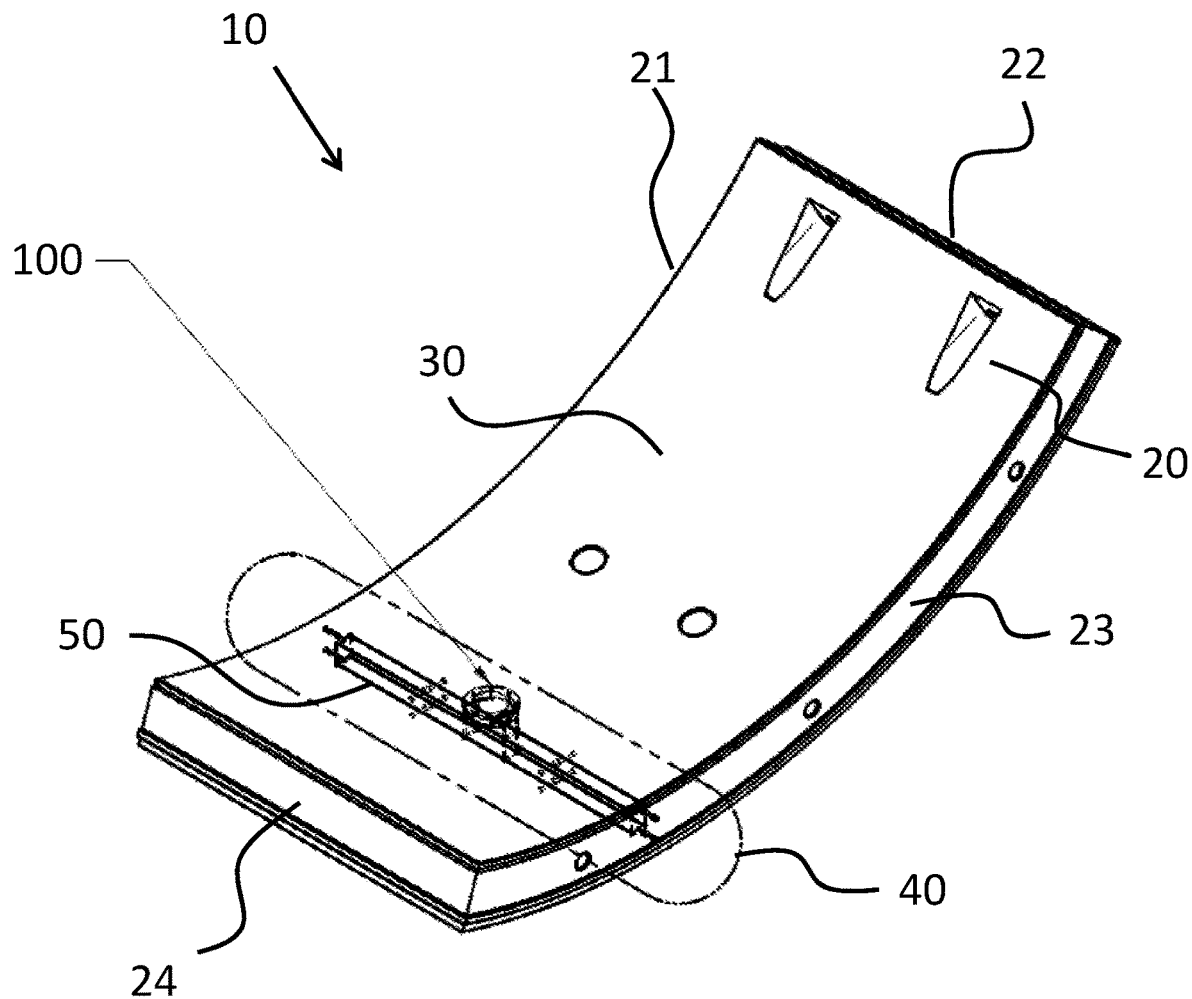
FIG. 1 is a schematic diagram of a concrete segment for use as a tunnel lining, the concrete segment including an embedded sensing apparatus.

FIG. 1 is an isometric view of a concrete slab or segment 10 intended for use in a tunnel, such as an underground (metro/subway) tunnel, e.g. as part of the London Underground network. It will be appreciated that such tunnels frequently have a generally circular cross-section (apart from a flat base or floor for supporting the track). We will refer herein to direction of travel through the tunnel as the longitudinal direction, the direction around the circumference or perimeter of the tunnel as the azimuthal or circumferential direction, and the direction from the centre of the tunnel out towards (and normal to) the walls of the tunnel as the radial direction.

The concrete slab 10 has two opposing and substantially parallel faces, an inner (intrados) face 30 and an outer (extrados) face (the latter not visible in FIG. 1), the inner face 30 being located radially inwards of the outer face. The slab 10 further has four side walls that join or span between the inner and outer faces. These four side walls comprise two pairs of opposing side walls; one pair of side walls 22, 24 extending in a substantially longitudinal direction, the other pair of side walls 21, 23 extending in a substantially azimuthal direction.

The concrete slab 10 is provided with a curvature in the azimuthal direction to match the shape (curvature) of the tunnel. The tunnel lining can then be formed from a set of concrete segments 10, with each concrete segment 10 extending around a portion of the circumference of the tunnel, with the inner and outer faces of segment 10 generally perpendicular (normal) to the radial direction of the tunnel. The segments may be provided with certain fixtures 20 which are used to help join the segments 10 together (usually at the point of installation). It will be appreciated that fixtures 20 are just one example of a method of attaching slab 10 to the inside of the tunnel, and other methods may be used as appropriate.

A tunnel may experience various changing conditions. For example, one problem in maintaining the structural integrity of tunnels is that material immediately outside the tunnel, such as soil, may be eroded (usually by water). This leaves a gap on the outside of the tunnel, which may impact the distribution of stress, etc. Furthermore, over the lifetime of the tunnel, the movement of trains or other vehicles through the tunnel may cause a gradual disruption to the tunnel shape. In addition, other nearby construction works, e.g. for building construction, may also impact the tunnel.

Consequently, as described herein, the tunnel slab 10 is instrumented with a sensing (monitoring) capability for detecting various types of movement, such as tilt and vibration. In particular, embedded within the slab 10, generally within the region indicated by dot-dashed line 40, is a sensing apparatus 100 (also referred to herein as a sensor assembly) which can be used to detect any such distortion. In this context, "embedded" implies that the sensing apparatus 100 does not protrude (radially inwards) from the slab (or at least any such protrusion is small compared to the size of the sensing apparatus 100 and the clearance required in the tunnel).

Such an embedded arrangement helps the sensor apparatus 100 to remain in position for a significant lifetime, as discussed below, including when trains or other vehicles pass through the tunnel. In particular, embedding the sensing apparatus within the slab 10 avoids or at least reduces the risk of the sensing apparatus being physically struck and/or damaged by a passing train (and potentially damaging the train as well). In addition, such embedding also helps to secure the sensor assembly 100 reliably within the segment 10, thereby reducing or avoiding the risk that the sensing apparatus might fall from the slab 10 (the tunnel lining) onto the train or track, for example, due to the very significant air turbulence caused by a passing train. It will be appreciated that any such fall is likely at least to stop the sensing apparatus working properly, and also has the potential to cause an accident (possibly serious) for the train. Furthermore, embedding the sensor assembly 100 in the slab 10 also provides more reliable monitoring of the concrete lining, in that the sensors 150 (as described below) are tightly coupled to (embedded in) the slab itself, rather than being directly exposed to turbulence or vibrations caused by passing trains.

Figure 2:
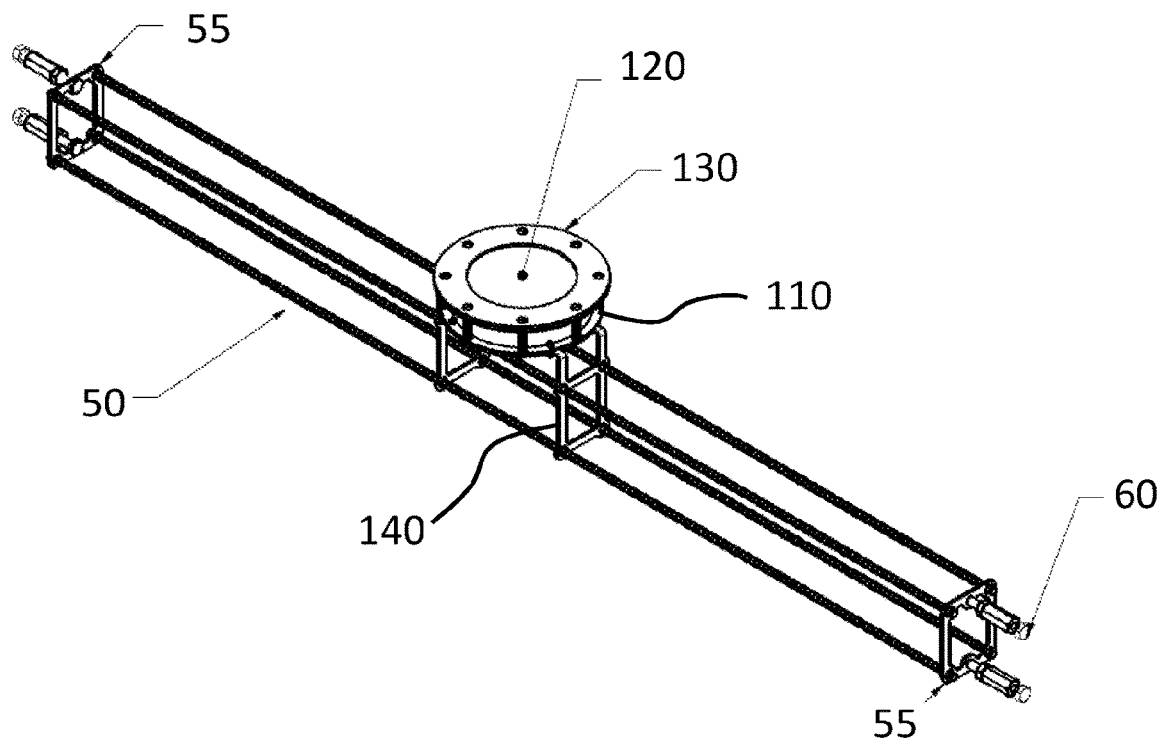
FIG. 2 is a schematic diagram of one example of the sensing apparatus of FIG. 1, prior to embedding in the concrete segment.
Figure 3:
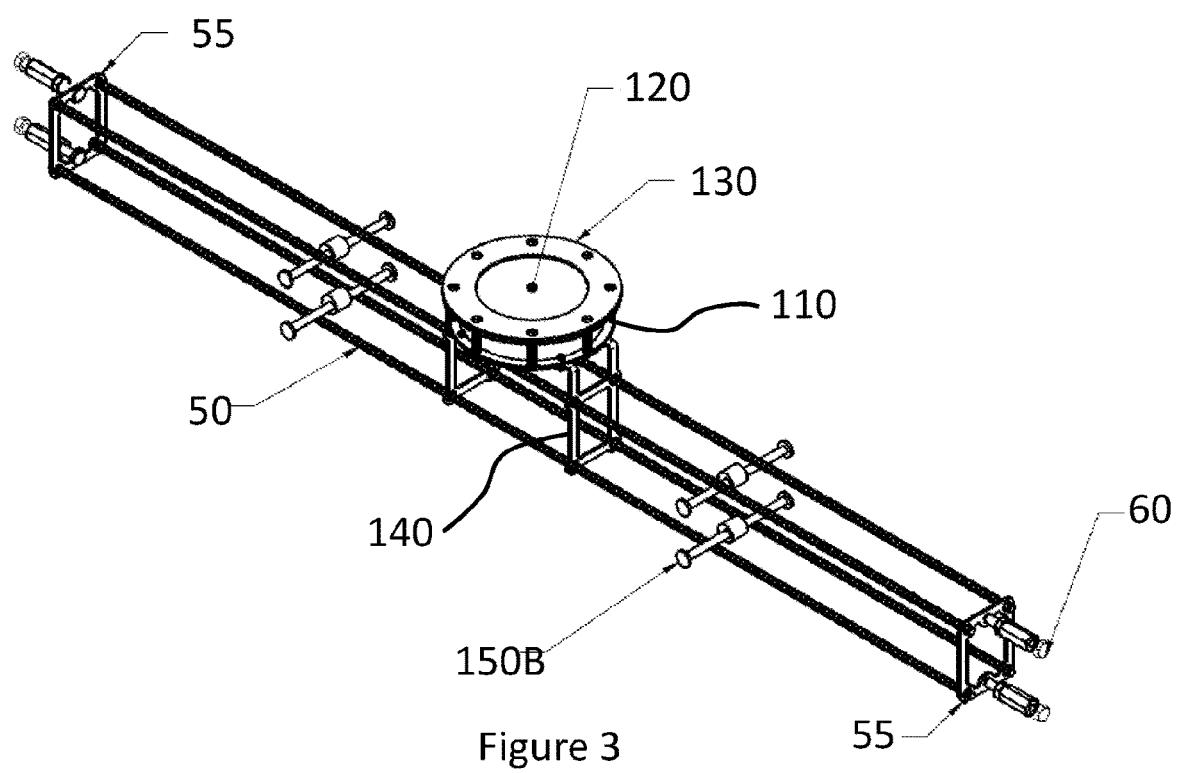
FIG. 3 is a schematic diagram of another example of the sensing apparatus of FIG. 1, prior to embedding in the concrete segment.

FIGS. 2 and 3 show two implementations of the sensor assembly 100 which may be embedded within a segment 10 of a railway tunnel, such as shown in FIG. 1. The sensor assembly 100 generally comprises a control system and a sensor 150. One or more bars (or other appropriate structure(s)) 50 are used to locate and retain the sensor assembly 100 within the concrete slab 10 (and also to reinforce the concrete slab). Typically the sensing apparatus 100 is provided with multiple sensors 150. In addition, although the control system of FIGS. 2 and 3 is contained within a single housing 110, in other implementations, this functionality may be distributed across multiple separate units.

In the sensor assembly 100 shown in FIG. 2, the sensor(s) 150 are all located within the housing 110 (and so not visible in FIG. 2). In the sensor assembly 100 shown in FIG. 3, there are multiple sensors external to housing 110, attached to bars 50 (there may also be one or more additional sensors 150 located within housing 110, not visible in FIG. 3). The sensing apparatus 100 generally contains at least the following within the housing 110: a wireless communication system (including an antenna to support wireless communications), a battery configured to provide power to the sensor assembly 100, and a processor unit (e.g. microcontroller) configured to control the operation of the sensing apparatus 100. As mentioned above, the sensing apparatus 100 may further include one or more sensors 150 within the housing 110. The sensing apparatus may also contain additional support components as required—for example, a storage (memory) facility for holding program instructions to be executed by the processing unit and/or to record (log) data from the sensors 150. This storage facility may be integrated, at least in part, into the other components as appropriate, e.g. the storage for data logging may be provided in conjunction with the sensors 150, and/or the program storage may be provided as part of the processor unit.

In the sensor assembly 100 shown in FIGS. 2 and 3, the enclosure or housing 110 has a generally cylindrical shape, with circular top and bottom faces, and a side wall extending around the circumference of the cylindrical shape. As installed into the concrete slab 10, the central axis of the cylindrical shape is aligned with (parallel to) to radial axis of the tunnel, so that the top face 120 of the enclosure (also referred to herein as the lid or cover) is generally parallel to the inner face of the concrete slab. In particular, the top face of the enclosure is typically flush with the inner face of the concrete slab 10 (or at least approximately so). As a result, the sensor assembly 100 is embedded within the concrete segment 10 such that the top face 120 of the housing 110 remains exposed and accessible, but does not protrude into the tunnel. This allows the exposed top surface to be used as a removable cover or lid 120, thereby providing access to the interior of the housing 110, e.g. for maintenance purposes. The remainder of the housing 110 (other than the lid), namely a base portion comprising the floor or bottom of the housing (opposite the lid 120) and the side walls, remains embedded within the concrete, and so cannot be removed.

Also visible in FIGS. 2 and 3 is a gasket 130, made of rubber, silicone, or any other suitable material for providing a seal between the lid 120 and the remainder of the housing to prevent the ingress of water, dust and/or other potential contaminants into the housing 110. (The gasket 130 also helps to protect the interior of the housing 110 from the intrusion of concrete during the formation of slab 10 around the sensing apparatus 100, as described in more detail below).

As shown in FIGS. 2 and 3, the housing 110, and also the sensors 150 which are external to the housing 110, are mounted on metal (most typically steel, e.g. mild steel) reinforcing bars 50 that extend through the concrete segment 10. In the particular implementation of FIGS. 2 and 3, there are four reinforcing bars 50 that extend parallel to one another, and are configured to lie at the corners of a square or rectangle (as seen looking along the length of the bars 50).

The bars 50 are held in this configuration by a pair of brackets 55, one bracket being located at each end of the bars 50.

It will be appreciated that such reinforcing bars (sometimes abbreviated to rebars) are widely used in reinforced concrete to provide mechanical strengthening for the concrete. Accordingly, bars 50, or some other appropriate structure, such as a mesh, fibres or grill, may conveniently serve not only as a reinforcing component for the concrete slab 10, but also as a facility for mounting and retaining the sensing apparatus 100 within the concrete slab 10. This approach helps to minimise the provision of additional components within the concrete slab 10 to accommodate the sensing apparatus 100 (since the rebars 50 or such-like would in any event generally be present in the concrete to act as a reinforcing structure). In addition, the rebars or other reinforcing structure(s) have already been designed and tested to remain securely in the concrete slab 10 for the lifetime of the segment, and so provide a stable and robust mounting facility for the sensing apparatus 100. Furthermore, the mounting of the sensor assembly 100 to the bars 50 (substantially) prevents movement of the sensor assembly 100 relative to the segment 10, hence the sensors 150 of the sensing apparatus reliably monitor movement and/or distortion of the segment 10 itself that contains the sensing apparatus 100.

In FIGS. 2 and 3, the enclosure 110 is mounted to the reinforcing bars 50 by a bracket 140. In the implementation of FIGS. 2 and 3, the bracket comprises a top portion, which is attached to the underside (lower face) of the enclosure 110 and then two opposing support portions that descend from the top portion and engage the four reinforcing bars 50. In particular, each of the opposing support portions is provided with four holes or slots to receive and retain a corresponding rebar 50. It will be appreciated that bracket 140 represents just one example of a suitable mounting device, and other fixtures or methods for mounting the enclosure 110 to the bars 150 will be apparent. In addition, in some implementations, the bracket 140 and enclosure 110 may be formed as a single unit which attaches directly to the reinforcing bars.

In the configuration of FIGS. 2 and 3, the underside of the enclosure 110 is mounted on the top portion of the bracket 140 by any suitable fixing, e.g. bolting or welding. Although the former would potentially allow the enclosure 110 to be subsequently removed from the bracket 140 if so desired, the concrete of slab 10 still generally acts to hold the enclosure 110 within the slab 10. Accordingly, the enclosure 110 is typically intended to remain in position for the lifetime of the concrete. However, the sensing apparatus is designed to that the operational components within the enclosure 110 can be repaired or renewed if required by opening (removing) the cover 120.

In the implementation of FIG. 2, all of the sensing apparatus 100, including sensors 150, are located within the enclosure 110 (the enclosure also being regarded as part of the sensing apparatus 100). In contrast, in the implementation of FIG. 3, the sensing apparatus 100 includes external sensors 150, which are themselves embedded within the concrete segment 10. These external sensors 150 are mounted directly onto the rebars 50; more particularly, each sensor 150 is fastened at each end to a respective rebar, so as to be located between (span) a pair of rebars. The sensors can be fastened to the rebars (or other supporting structure) by any appropriate fixing device, for example, tie dips, screws, etc.

A wired connection (not shown in FIG. 3) is provided between each external sensor 150 and the control system in the enclosure 110, firstly to allow the control system to provide power to the external sensors, and secondly to allow the control system to retrieve the sensed data from the external sensors (and to send command instructions if required). Each wired connection is provided within a sheath or other form of wrapping or cabling to protect the wired connection, which runs internally within the concrete of the slab 10. This sheathing also protects the wiring at the time of forming the concrete slab, before the concrete has set.

In the particular implementation of FIG. 3, there are four external sensors 150 that measure strain within the concrete segment 10—these are embedded directly within the concrete itself, rather than being located within the housing 110. It will be appreciated that other implementations may have a different number of external sensors, for example, between 1 and 16 sensors, and or between 2 and 8 sensors; may comprise a different type of sensor; and/or may comprise more than one type of sensor, e.g. strain, tilt, vibration and/or moisture detectors. In addition, although the strain sensors of FIG. 3 are all in parallel, i.e. have the same orientation, in other implementations, the strain sensors may have differing orientations.

In production of a concrete slab 10 including sensing apparatus 100, the sensing apparatus is mounted onto the bracket 140 and then onto the rebars 50 (although in some cases the bracket 140 may be mounted first onto the rebars, and then the sensing apparatus 100 mounted onto the bracket 140). Mounting the sensing apparatus 100 onto the rebars includes fixing any external sensors 150 to the rebars, as discussed above. The wired connections between the external sensors and the enclosure may then be formed; in some cases, for protective reasons these wired connections are not completed until just before formation of the slab (see below).

Depending upon the particular design, mounting the sensing apparatus onto the rebars may be performed before, after, or at the same time as forming the configuration of rebars using brackets 55. The brackets 55 are provided with mounting bolts 60 for mounting the rebars into a slab mould (this mounting into the slab mould may be performed before, after, or at the same time as, the sensing apparatus 100 is mounted to the rebars).

With the sensing apparatus 100 mounted onto the rebars 50, including any external sensors 150 being wired to the enclosure 110, and with the rebars mounted into the slab mould, the casting process can now be performed, whereby the concrete is poured into the mould. After the concrete has set, the mounting bolts are removed to allow the slab 10 to be taken from the mould. The concrete slab 10 is then ready for installation into the tunnel, typically by using a vacuum erection process.

The inclusion of sensing apparatus 100 therefore makes relatively little difference to the (otherwise existing) process of producing and then installing the concrete slab. For example, if the sensing apparatus 100 is first mounted onto the rebars 50 (or other reinforcing structure), and the wired connections completed between the sensors and the enclosure, then the remaining steps of mounting to the slab mould, casting, and installation are generally the same as for a slab that does not include the sensing apparatus 100. It will be appreciated that this commonality of procedure can help to reduce costs and complexity.

Figure 4:
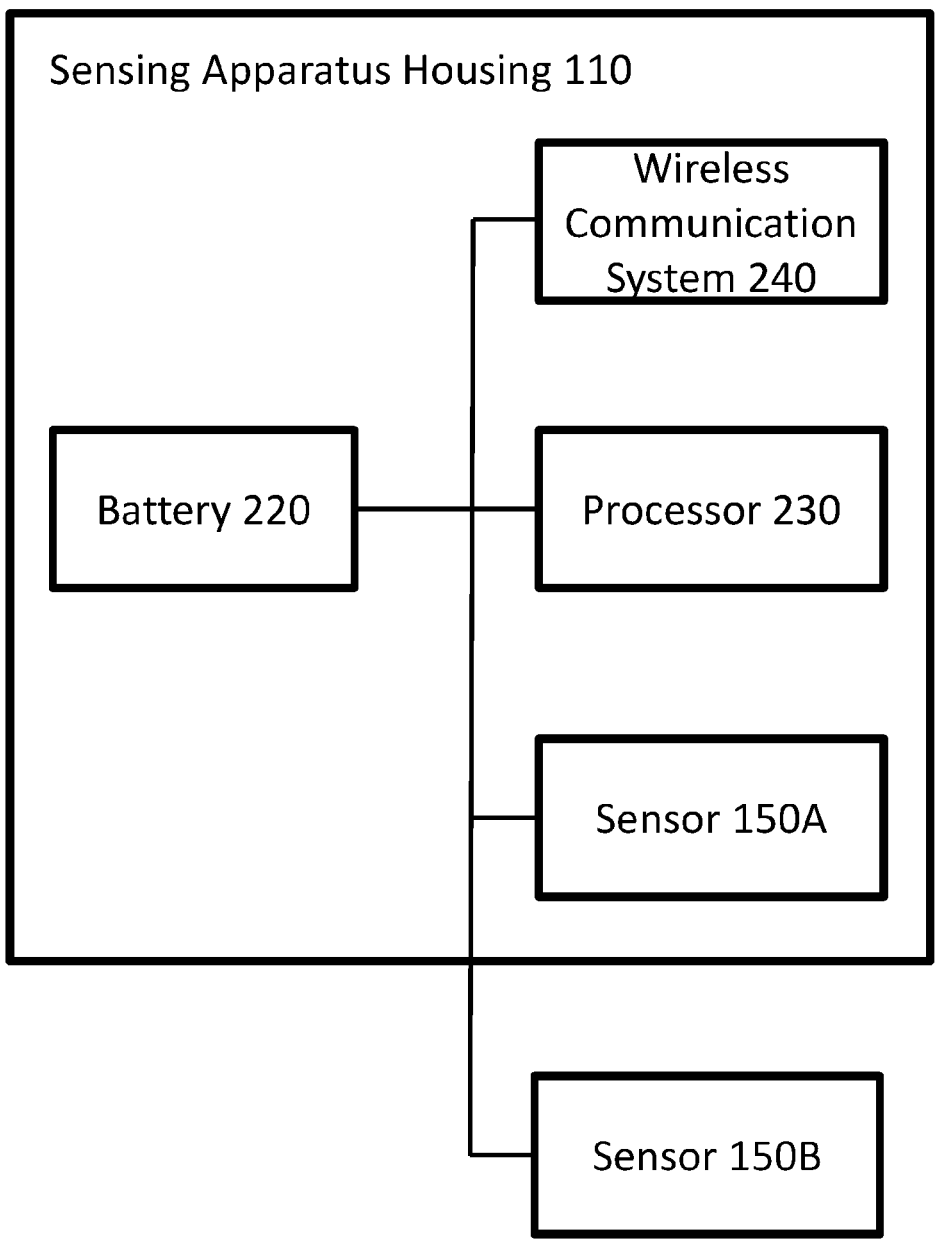
FIG. 4 is a schematic diagram of the main electrical and electronic components of the sensing apparatus of FIG. 3.

FIG. 4 is a schematic diagram showing an example of the electronic components in the sensor assembly 100 shown in FIG. 3. As discussed above, the sensing apparatus 110 comprises a housing 110 (the cylindrical enclosure) containing a control system comprising (at least) a battery 220, a processor unit 230 (such as a microcontroller), and a wireless communications system 240. The sensing apparatus 100 shown in FIG. 4 includes at least one sensor 150A within (internal to) the enclosure 110 and at least one sensor 150B outside (external to) the enclosure 110. By way of example, the internal sensor 150A may comprise a tilt sensor to measure rotation of the sensing apparatus 100 (and hence the concrete segment 10) about at least two axes. Such a tilt sensor may comprise an accelerometer and/or an electro-level sensor, and may be fabricated, in some implementations, as a MEMS (micro-electro-mechanical system) sensor. As discussed above, the external sensor 150B may comprise a strain sensor.

The lines linking the components in FIG. 4 indicate (schematically) electrical connections for power and/or data transmission as appropriate. Thus it can be seen that each component of the sensing apparatus 100 is connected to the battery 220 to receive a power supply. Note that in some implementations, one or more components may not receive power directly from the battery, but rather indirectly via the processor; this approach can potentially give the processor 230 more control over power usage by the other components.

FIG. 4 also shows the sensors 150A, 150B and the wireless communication system 240 all linked to the processor for data communications. The microcontroller 230 controls, inter alia, data sampling by the sensors, data communications to/from the sensing apparatus 100, and the overall timekeeping of the sensing apparatus. The output (sensed data) from each sensor 150 is transmitted to the processor unit (microcontroller) 230 (potentially this transmission path may involve an analog-to-digital (ADC) converter, depending upon the nature of the output from the sensor 150). In some cases the power and data may be provided over a shared link, for example, the data may be communicated using frequency modulation on a power transmission line; in other cases, there may be separate power and data lines. (It is also possible to use wireless links between the components for power supply and/or data communication, for example, via induction, however, these will generally be less attractive than wired links for reasons of cost and energy conversation).

In some implementations, the communication lines of FIG. 4 may also be used for sending control instructions to various components. For example, the processor 230 may direct various commands at sensors 150A, 150B, such as to poll (collect) the sensed data, or to change the sampling rate or some other configuration parameter, etc of the sensor 150. As noted above, in some implementations, the processor may also control when power is provided to the sensors 150.

The wireless communication system 240 is used to transmit the output of the sensor(s) 150 from the sensor assembly 100, e.g. to a base station, and likewise to receive command instructions into the sensor assembly 100, for example, to configure the processor 230; such instructions may then cause the processor to (re)configure other components in the sensing apparatus. In addition to transmitting data/instructions to/from the sensing apparatus 100, the wireless communication system 240 also allows the sensing apparatus 100 to act as a node in a wireless mesh network with other sensor assemblies 100, as described below.

The wireless communication system 240 includes an internal antenna to support wireless communications and circuitry to support the transmission and receipt of signals via the antenna (for example an RF module). In one implementation, the sensor assembly 100 communicates at a frequency of 2.4 GHz within the ISM (industry, scientific and medical) band in compliance with IEEE 802.15.4. The data rate is 250 kbits per second, with a typical duty cycle of 1%. The point-to-point range between one sensor assembly 100 and another transmitter/receiver is typically of the order of tens of meters. It will be appreciated these communication parameters are provided by way of example only, and other implementations may use different parameters and/or any other suitable wireless communications protocol. For example, a lower transmission frequency might be utilised for installations having a relatively low data transfer rate.

The battery 220 in the sensing apparatus 100 provides power to support the operational activities of the other components in the sensing apparatus. By way of example, the battery 220 may comprise a Lithium Thionyl Chloride ER34615 D cell from Eve (see http://en.evebattery.com/. This non re-chargeable battery has a nominal capacity of 19 Ampere hours and also a non-flammable electrolyte (unlike some other forms of lithium-based batteries). The battery supports low current draw over a long life-time. The electrical components within the sensing apparatus 100 generally have low energy requirements, so this battery is able to provide an operational lifetime of over 10 years, typically between 10 and 18 years, e.g. approximately 15 years. It will be appreciated that this timescale corresponds with many standard tunnel maintenance regimes, in other words, the lifetime of battery 220 is sufficiently long that the battery can be replaced as part of existing scheduled maintenance operations. Other types of battery with other properties may be used as appropriate.

The long lifetime for the battery 220 is helped because sensor readings may only be taken periodically, for example, every N hours, where N is typically between 0.5 and 200, more typically between 1 and 50. Note that in some implementations, N may be configurable during the lifetime of the sensing apparatus, e.g. by sending appropriate commands to the sensing apparatus 100 via the wireless communications system 240. When no sensor data is being acquired, the sensors 150 only draw a very small current, of the order of a few microamps. The microcontroller 230 is also put into a very low power (dormant) mode for most of the time when no data is being sensed or transmitted, and in this state the microcontroller 230 likewise draws a very small current, again of the order of a few microamps.

Note that a current of 10 microamps drawn over a continuous period of 11.4 years corresponds to charge of 1 Ampere hour. Given that battery 220 has a charge capacity of approximately 19 Ampere hours, it can be seen that current draw while the device is inactive may consume only a relatively low percentage (~5%) of the total battery capacity (although this figure will vary according to the particular design of the sensor assembly—e.g. having more sensors 150 installed in the sensing apparatus 100 will tend to increase the current draw).

The wireless communication system 240 is a relatively significant energy consumer within the sensing apparatus 100. In some systems, such as the IEEE 802.15.4 implementation discussed above, time synchronisation can be utilised to minimise the energy consumption of the wireless communication system 240. In this implementation, each sensing apparatus 100 (and more particularly the wireless communication system 240 therein) can act as a node in a distributed mesh radio communication network. Each node is only in active communication over the network for a relatively short fraction of overall time (i.e. the duty cycle is low). Rather than listening or monitoring all the time for potential new communications, the nodes agree a schedule for sending and receiving new transmissions. The wireless communication system 240 is synchronised with this schedule, and hence with the other nodes in the network. Accordingly, at an appropriate time as specified by the schedule, the wireless communication systems 240 of multiple nodes switch on (become active) together, thereby forming an active network to support data communication across the network—and ultimately to/from a base station or gateway, which can be used to interface with external networks, such as the Internet, or a local area network supported within certain locations of the tunnel.

It will be appreciated that this synchronised approach is energy efficient, because the nodes only seek to form network connections when other nodes are also available and likewise also seeking to form network connections. This therefore allows rapid set-up of the network connections, thereby allowing the desired communications to be performed over the network, after which the sensor assemblies 100 that form the different nodes can return to a dormant (energy-saving) mode.

In addition, the spacing between the different sensor assemblies 100 within the network is generally less than the transmission range of the wireless communication system 240—hence a given sensor assembly is likely to be able to communicate with multiple other sensor assemblies in the tunnel. Accordingly, the resulting communication network has a mesh configuration, with multiple independent paths available across the network. This multiplicity of paths provides redundancy, in the sense that network communications are still available even across a subset of the nodes. This redundancy helps to avoid communication problems if any given node fails (for nodes other than the failed node). In addition, the redundancy allows the network to be implemented at a given time across only a subset of the nodes, thereby allowing the other nodes to remain in a dormant (low-power mode).

Figure 5:
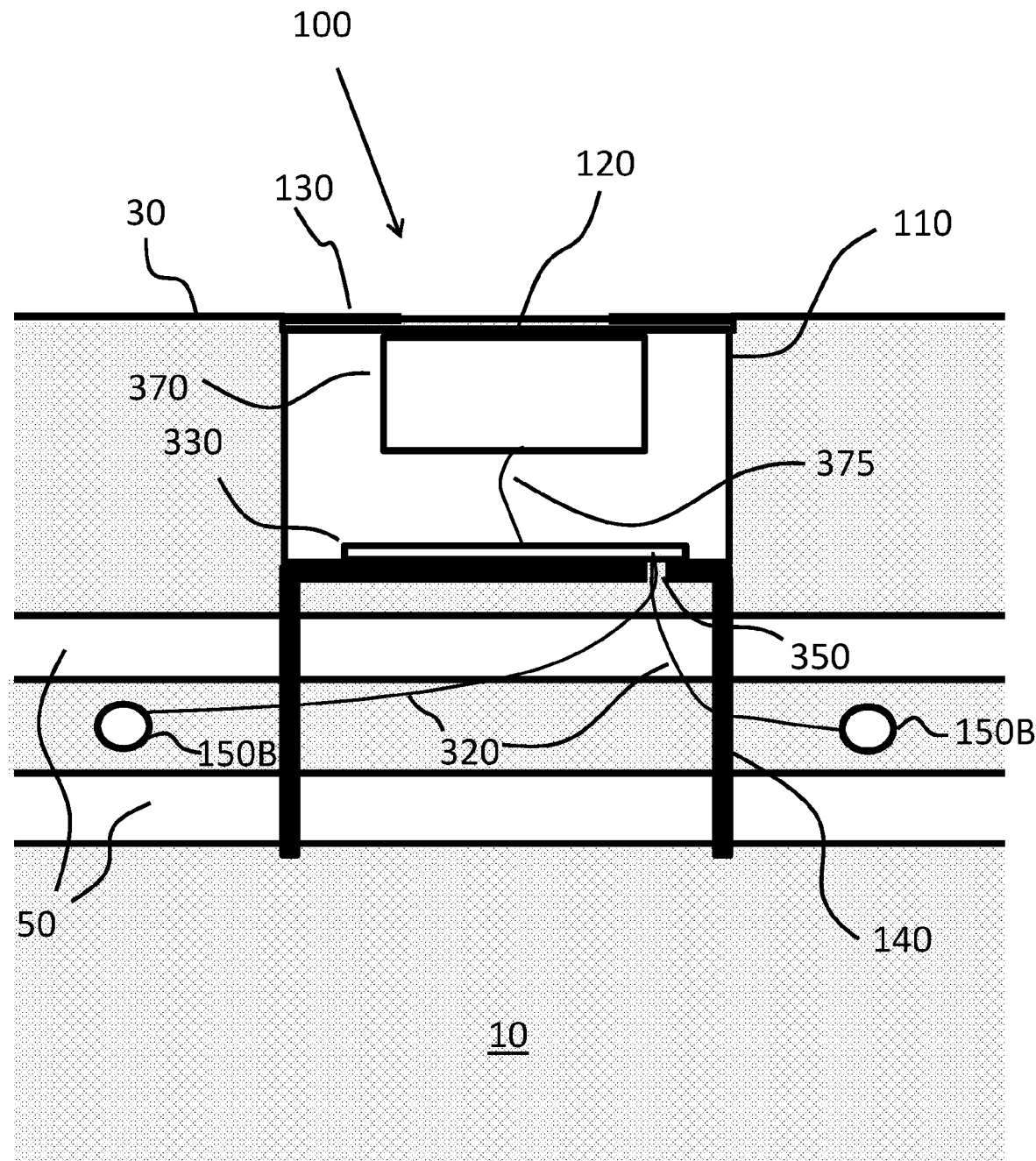
FIG. 5 is a side view of the sensor apparatus of FIG. 3 embedded in a concrete segment.

FIG. 5 provides a schematic side view, perpendicular to the longitudinal axis of the rebars 50, of a sensor assembly 100 embedded in a concrete segment 10 in accordance with the examples of FIGS. 3 and 4. The component dimensions, relative sizes and position are very approximate, and shown only for illustration; it will be appreciated that other implementations may have different configurations according to the particular design objectives of any given implementation.

FIG. 5 shows the sensor assembly 100 comprising a housing or enclosure 110 and two external sensors 150. The housing 110 is mounted on a support 140 embedded within the concrete segment 10. As discussed above, in some implementations the enclosure 110 is cylindrical, but may have any suitable desired shape—e.g. a rectangular (box-like) shape, hexagonal, etc. For robustness and longevity, the housing is normally 110 made of stainless steel or cast iron, however, other materials such as plastic might be used instead. The enclosure is provided with a removable lid or cover 120 on the top (exposed) surface. The remaining portion (base or body) of the housing 110 may be constructed as a single component, for example a cast iron container, or may be constructed from multiple components, for example a section of steel pipe fitted with a circular plate at the bottom (and the lid or cover 120 at the top). The lid 120 may be attached to the housing base using any suitable fixing mechanism that supports removability. For example, the lid may be attached to the base by bolts, or may be provided with a thread to screw directly into the base. The top of the enclosure is also provided with a gasket 130 which sits flush with the inner face 30 of concrete segment 10. The gasket 130 may be made of any suitable resilient material, such as rubber or silicone, which is able to form a seal and so provide good environmental protection and oil/grease resistance for the sensing apparatus 100. Another gasket (not shown in FIG. 5) may also be provided at the bottom of the enclosure (if the base or floor is formed separately from the sidewalls of the enclosure 110). For example, the gasket may be made of synthetic rubber, such as ethylene propylene diene monomer (EPDM) (M-class) rubber (this material is already used within existing concrete slabs 10 for other purposes).

The main internal components of the housing 110, as shown in FIG. 4, i.e. the microcontroller 230, the sensor(s) 150A, the battery 220 and the wireless communication system 240, may be mounted on the inside (underside) of the lid 120 (rather than on the base of the housing). The internal components are depicted collectively (and schematically) by reference numeral 370 in FIG. 5. Having internal components 370 mounted on the lid 120 supports quick removal of these components for inspection, testing, replacement, etc. as required, in that when the lid 120 is detached from the body of the enclosure, the components 370 are extracted with the lid. In some cases, the lid 120, including the attached components, may be removed completely from the base or body of the enclosure 110 and replaced by a new lid which is fitted with corresponding components—e.g. updated electronics and a new battery. It will be appreciated that such a service operation is straightforward to perform in the field, without having to worry about the detailed internal configuration of the sensing apparatus 100.

If the sensing apparatus 100 includes one or more external sensors 150B embedded in the concrete segment 10 outside the housing 110, such as shown in FIG. 5, then these are connected to components within the housing 110 via wiring 320. The external wiring 320 shown may comprise a bundle of wires surrounded by a protective sheath or similar and support the transmission of power, data and commands as appropriate between the external sensors 150B and the enclosure 110 (and the components therein). In some implementations, the external sensors 150B comprise vibrating wire strain gauges, which are also used to monitor other forms of concrete structures with steel reinforcing, such as dams, and have a long operational lifetime (comparable with the lifetime of the concrete segment 10 in which they are embedded). For example, the vibrating wire strain gauges may be a vibrating wire embedment strain gauge (http://soil.co.uk/products/strain-gauge/vibrating-wire-embedment-strain-gauge/available) from Soil Instruments (see www.soil.co.uk). Other forms of vibrating wire strain gauge could also be used, for example, from the same supplier, including a vibrating wire sisterbar/rebar strain gauge (http://soil.co.uk/products/strain-gauge/vibrating-wire-sisterbarrebar-strain-gauge and/or a vibrating wire arc weldable strain gauge (http://soil.co.uk/products/strain-gauge/vibrating-wire-arc-weldable-strain-gauge/). Such strain gauges are typically fixed directly to the rebars, and can be provided to be sensitive to strain in multiple directions. Note that this type of vibrating wire strain sensor generally has a longer expected lifetime than some other forms of strain gauge, such as a foil strain gauge.

The enclosure is provided with a simple (dumb or passive) standard connector or terminal module 330 for receiving wiring 320 into the housing 110. (If there are no external sensors 150B, the terminal module 330 may be omitted, since in this case there is no external wiring 320 to receive; in addition, any internal sensor 150A is generally connected directly to the other internal components, such as battery 220, since they are jointly mounted together on the lid 120).

The terminal module 330 is then in turn linked to the other (active) electrical and electronic components 370 within the enclosure, such as the battery 220 and the microcontroller 230 by wiring 375. The terminal module may be implemented on a simple printed circuit board (PCB) 330 which has no additional functionality, other than to provide this electrical connectivity, i.e. to act as an interface between the components 370 internal to the enclosure 110 and the external sensor(s) 150B. In some implementations, the wiring 375 from the other electrical and electronic components 370 within the enclosure is terminated by a terminal module that plugs into PCB 330 (rather than each internal component having its own separate connection to the PCB 330). Accordingly, during a maintenance operation in which the lid 120 supporting the internal (active) electrical and electronic components 370 is to be removed and replaced with a new lid (supporting new components), the terminal module at the far end of wiring 375 from the components 370 supported by the lid is first disengaged from PCB 330. This is a relatively straightforward action, e.g. to unplug the (single) terminal module from the PCB 330 (there is no need to unplug the terminal module from the external sensors 150B since these are embedded in the concrete, and hence cannot be replaced). Similarly, to install the new lid with the new internal components, there is likewise the relatively straightforward action of engaging (e.g. plugging in) the terminal module for the new internal components with PCB 330. Overall therefore, the use of PCB 330 to provide a single interface between (i) the external sensor(s) 150B, and (ii) the internal electrical and electronic components 370 of the enclosure 110 supports rapid replacement and renewal of the lid 120 (and associated internal electrical and electronic components) without having to perform any significant re-wiring. Furthermore, since the PCB 330 provides no more than dumb or passive electrical connectivity to the external sensors 150B, there is little likelihood of needing to upgrade or modify the PCB 330 in the future. Accordingly, the circuit board 330, the external wiring 320 and the external sensors 150B are typically installed for the life of the sensing apparatus 100 and concrete slab 10 within the tunnel, which may be many tens of years. Alternatively, in some implementations, the PCB 330 might also be removable, or may potentially be omitted, with wiring 320 plugging directly into (and likewise unplugged from) the internal components 370 as appropriate.

The housing 110 and, if appropriate, the support 140, may comprise one or more openings (gland holes) 350, to allow the wiring 320 from the external sensors 150B to pass into the housing 110 (e.g. for connection to the PCB 330). In the example of FIG. 5, there is one gland hole 350 located in the underside of the housing 110, however, in other implementations, there may be multiple such gland holes, and one or more of the gland holes may potentially be formed in the side wall of the enclosure (rather than in the base). The gland hole (s) are typically providing with appropriate sealing to prevent or minimise any ingress of contaminants into the interior of the housing 110 (especially during the casting process of slab 10). Such sealing may initially be applied before the wire(s) 320 are connected between the external sensors 150B and the PCB, and then additional sealing may be applied to the gland hole(s) 350 after the wires 320 have been fitted. Note that this additional sealing may be a protective resin or similar which sets hard to seal the hole 350 in a permanent manner (since as discussed above, the wires 320 are expected to remain in place for the lifetime of the sensing apparatus).

Figure 6:
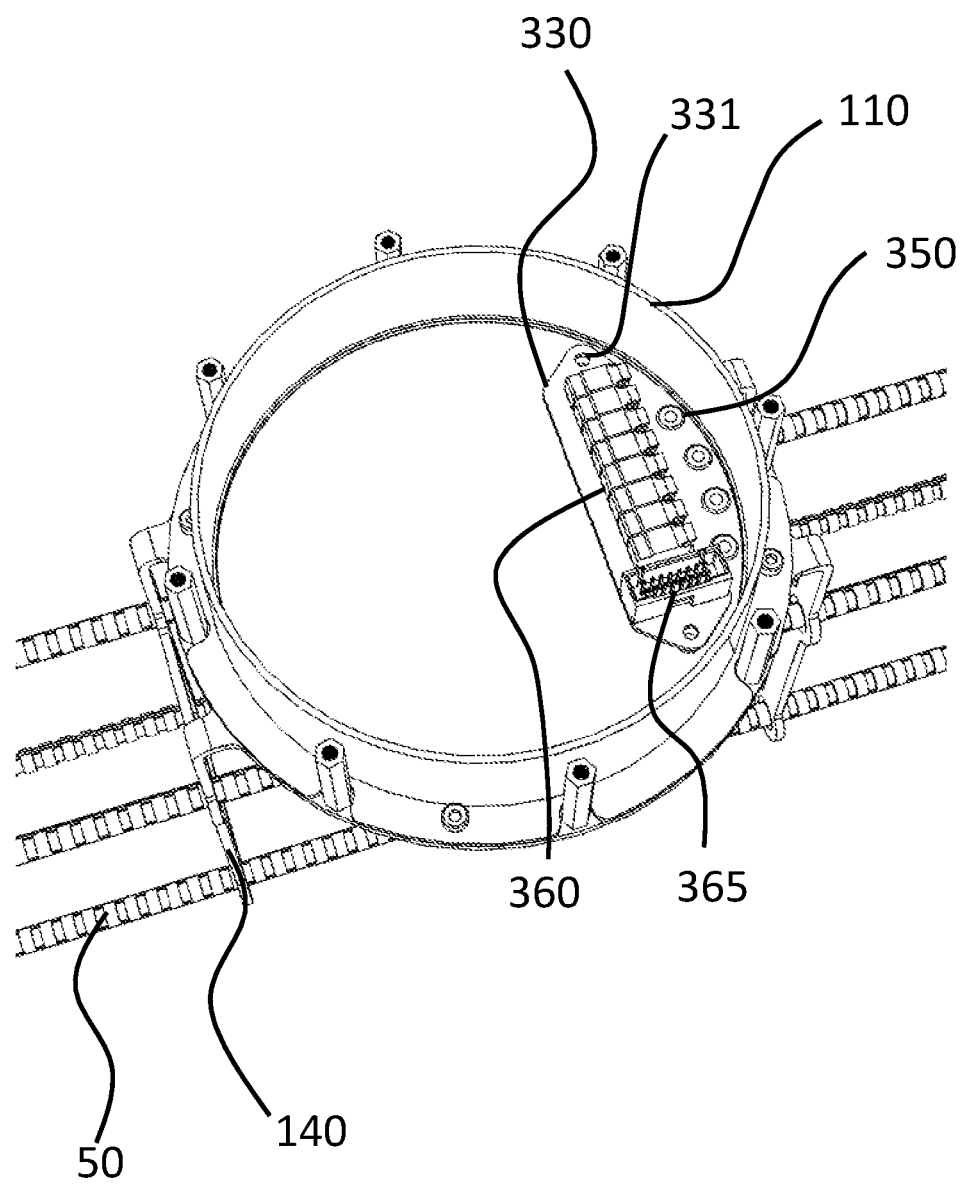
FIG. 6 shows a view of the sensor apparatus 100 of FIG. 5 with the lid removed.

FIG. 6 shows a view of one implementation of the sensor apparatus 100 of FIG. 5 with the lid 120 removed. The sensor assembly 100 comprises the enclosure 110 (without the lid 120) mounted to reinforcing bars 50 by support 140. As discussed above, the support 140 attaches to both the reinforcing bars 50 and the enclosure 110 to hold the enclosure 110 in position with respect to the reinforcing bars 50. Gland holes 350 are provided through the base surface (floor) of the enclosure 110 to allow cabling 320 to pass from the enclosure 110 to external sensors 150B (the cabling and external sensors are not shown in FIG. 6). As discussed above, the gland holes 350 help to maintain the waterproof or dustproof nature of the enclosure 110.

The enclosure 110 includes the terminal module in the form of a PCB 330, which is provided with a hole 331 at each end for attachment to the base (floor) of the enclosure, e.g. using a screw fitting. The PCB 330 may therefore be removable from enclosure 110 should the need arise, even though the intention may be, as mentioned above, for the PCB 330 to remain in the enclosure for the operational lifetime of the sensor assembly 100. The PCB 330 supports a first terminal module 360 and a second terminal module 365. The first terminal module 360 is used to receive cabling 320 from the external sensors 150B via the gland holes 350. For example, first terminal module 360 may comprise a set of clip or screw contacts for attaching the conducting wires 320 from respective sensors 150B. The second terminal module 365 may comprise a male or female terminal module with suitable pins or holes for receiving a complementary terminal module located at the end of wiring 375 from the internal components 370. The PCB then provides appropriate connectivity between the first terminal module 360 and the second terminal module 365 to support electrical transmissions between the internal components 370 and the external sensors 150B.

While FIG. 6 shows four gland holes 350, it will be appreciated that in other examples there may be a different number of gland holes 350 (which may be differently configured, etc). In some examples the number of gland holes 350 may correspond to the number of external sensors 250; however in other examples a single gland hole may provide wiring to more than one external sensor. In some implementations, the gland holes may be replaced by another facility to provide electrical connectivity into the enclosure 110, e.g. a suitable terminal module may be formed or provided directly in the wall itself of the enclosure 110.

As discussed above, in some implementations, the wireless communication systems 240 in respective sensor assemblies 100 support the formation of a mesh communications network, in which the sensor assemblies form the nodes of the network. The network allows all the nodes in the network (i.e. all the sensor assemblies) to send communications to and receive communications from a desired system—e.g. a base station, a control unit, a gateway systems, wireless access point etc.

Figure 7:
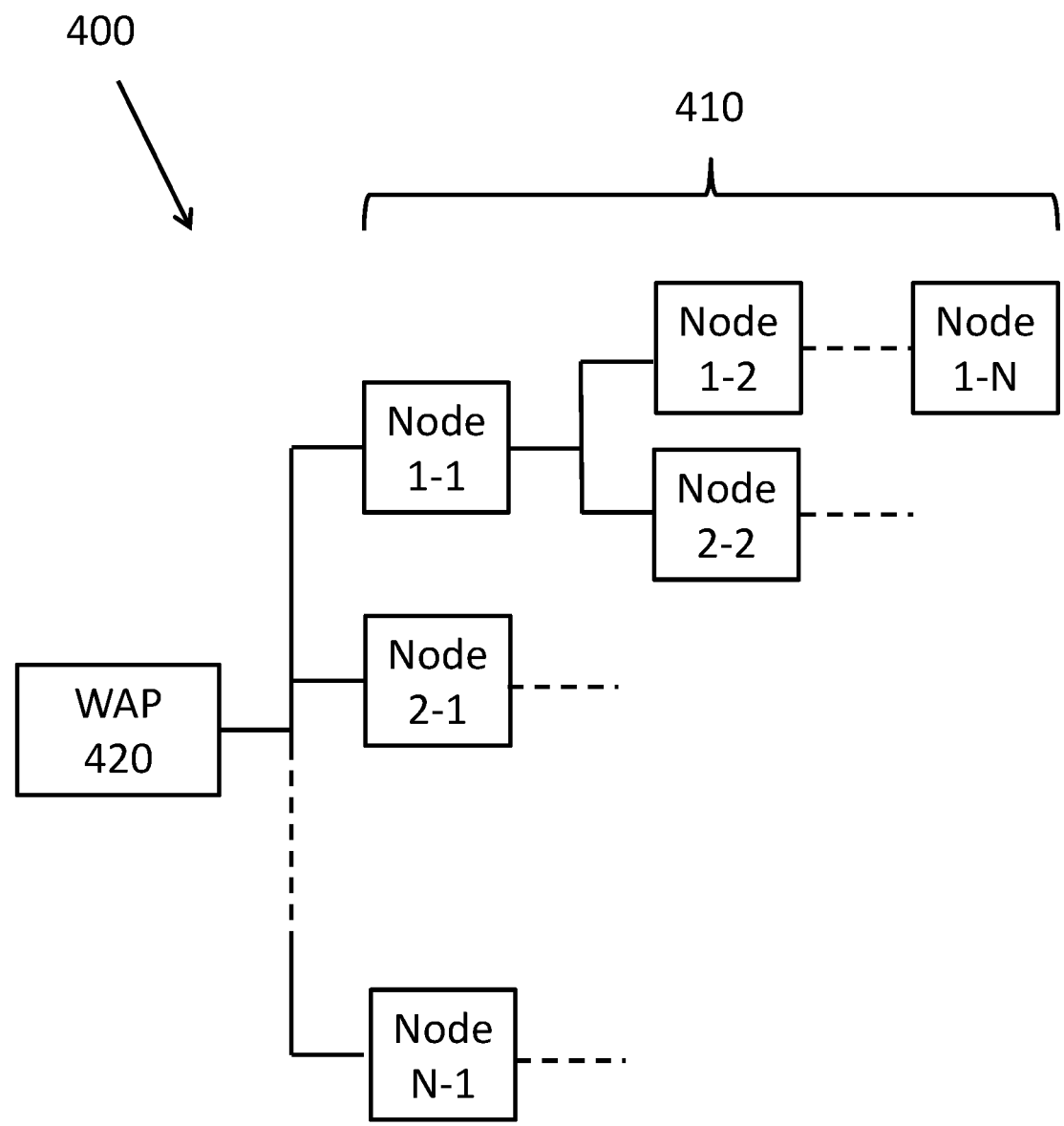
FIG. 7 is a schematic diagram of multiple sensor assemblies such as shown in FIG. 4 configured as a mesh network.

FIG. 7 is a schematic diagram of an example of such a mesh network 400 formed by sensor assemblies 100 acting as nodes 410 within the network. Rather than each individual sensor assembly 100 communicating directly with a wireless access point 420, such communications may travel across multiple nodes in the network. Thus in the configuration shown in FIG. 7, nodes 1-1, 2-1 ... N-1 communicate directly with wireless access point 420, but other nodes communicate with the wireless access point 420 indirectly (i.e. via other nodes). For example, nodes 2-2 and 1-2 communicate with the wireless access point 420 via node 1-1, i.e. node 1-1 acts as an intermediary for communications between the wireless access point 420 and nodes 1-2 and 2-2, so that communications between the wireless access point 420 and nodes 1-2, 2-2 pass through (are relayed by) node 1-1. Moreover, node 1-2 may itself act as an intermediary, relaying communications along a chain or path of other nodes (this path is indicated schematically in FIG. 7 using dashed lines as extending to node 1-N via one or more other intervening nodes, not shown in FIG. 7). Further implementation information about the use of wireless communications to form sensor networks can be found in "Wireless Sensor Network Survey" by Yick et al, in Computer Networks, Volume 52, Issue 12, 22 Aug. 2008, pages 2292-2330 (and in the citations thereof).

This use of a mesh network helps to save power, because it reduces the maximum transmission distance that has to be supported by any given sensor assembly (each node only needs to support direct communications with its nearest neighbour node(s), not with the wireless access point itself). This also reduces the overall power requirement for the network 400 as a whole. Thus if D represents the distance between a given node 410 and the wireless access point 420, we can write D≈NL, where N is the number of hops or legs (between nodes) required to span the distance D, each hop being of length L. In this approach, the overall power requirement scales linearly with N, but generally with the square of L.

The particular network (node) configuration shown in FIG. 7 is a tree network, in which each node 410 has only a single path to the wireless access point 420. However, other network configurations may be used, in which a node may have multiple different paths to connect to the wireless access point (or other desired location). These multiple network paths may be used to provide redundancy/resilience, i.e. the ability to continue communications over an alternative path if a node or link fails on one particular path. Accordingly, the use of a mesh network 400 for connecting the sensor assemblies 100 provides a robust communications architecture. Even if one path goes down, for example because a given sensor assembly fails or because of the presence of an obstacle, the nodes may be able to maintain communications via an alternative path through the mesh network.

The nodes 410 may be self-configuring to form network 400, i.e. once installed and switched on, they do not need manual configuration to form the mesh network, but rather form the network automatically via a process of node discovery. The mesh network may also support dynamic reconfiguration, such as when one or more sensors are added to or removed from an existing network, e.g. as new segments are added to the tunnel construction or during refurbishment. This dynamic reconfiguration may result in the network 400 forming new links between nodes 410 (sensor assemblies 100); conversely, the reconfiguration may result in the network ending links that are no longer operational—for example, because one of the sensor nodes involved in the link has been removed or switched off. Again, it will be appreciated that such dynamic reconfiguration in terms of the wireless communications occurs automatically (it does not have to be manually controlled by an operator).

Accordingly, a wireless mesh sensor network such as described herein provides great freedom and flexibility in how the sensor assemblies 100 may be deployed. For example, support for dynamic reconfiguration of the wireless mesh sensor network allows the sensor network to be actively updated as engineering work (segment installation) progresses along the tunnel. Furthermore, as described earlier, time synchronisation may be utilised to minimise the energy consumption of the wireless communication system 240 of each node of the mesh network. A schedule for controlling such synchronisation may be dynamically updated (and distributed) according to the addition (or removal) of nodes to (from) the mesh network.

FIG. 7 shows the wireless network 400 terminating at a wireless access point 420, which may link to a local computer—and from there to a wide area network, such as the Internet. In another implementation, the wireless access point may serve as a gateway to a GPRS (general packet radio service) link. The skilled person will be aware of other potential forms of connectivity for the wireless access point (or other forms of termination for the network 400). In addition, some mesh networks may connect to multiple endpoints, e.g. to multiple wireless access points.

In most tunnel installations, the wireless network 400 is primarily formed to provide communications along the length of the tunnel (the longitudinal axis). In other words, a wireless access point 420 is located at one position along the tunnel, and the sensors are placed in locations along the tunnel extending away from the wireless access point 420. The mesh network 400 then supports communications along the tunnel, potentially over distances of hundreds of meters, or multiple kilometres, between the sensors (nodes 410) and the wireless access point 420.

It will be appreciated that the provision of a battery 220 in each sensor assembly 100 and the use of the wireless mesh network 400 for communications avoids the need for an existing (or new) wired infrastructure to provide power and/or data communications to the sensor assemblies 100. Instead, the sensor assemblies 100 are installed into their respective slabs 10; the slabs can then be installed into the tunnel using a conventional process, without having to provide any additional wiring connections, etc. At most, an operator has to provide at least one wireless access point (or similar) within range of the overall mesh network (and even if such a wireless access point is not already available, it is generally much simpler to introduce this single access point than it is to provide a wired connection to each individual sensor assembly 100).

Although the wireless network 400 described above is a mesh network based on IEEE 802.15.4, other forms of network can be used as appropriate. For example, different forms of network configuration might be adopted, such as a star network, a spanning tree, etc. Likewise, different frequency bands (compared with IEEE 802.15.4) and/or communication protocols might be adopted. For example, the data rate from the sensor assemblies 100 is relatively low, which would enable a lower frequency network to be used if desired.

Figure 8:
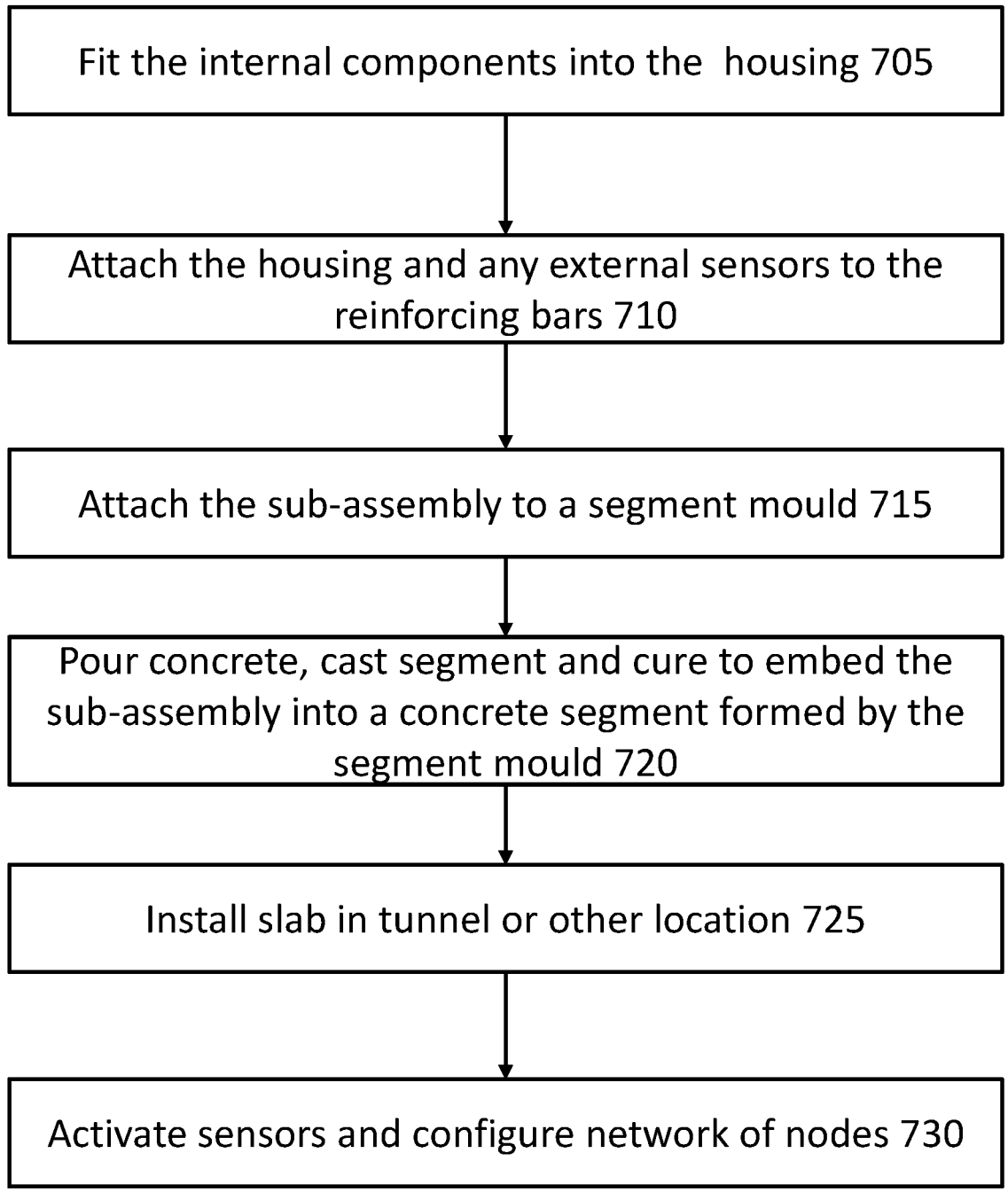
FIG. 8 is a flow diagram of an example method for forming and installing the sensor assembly as described herein.

FIG. 8 is a flow diagram showing an example of a method for installation of a sensor assembly 100 such as described herein. Initially at operation 705, the internal components 370 are fitted inside the housing 110, and likewise any external sensors are wired up as required to the internal components. As mentioned above, the internal components 370 may be mounted on the lid 120 of the enclosure for ease of such fitting. The process continues at operation 710 with attaching the housing 110 and the external sensors 150B (if any) to the reinforcing bars (rebars) 50. As described above, the attachment of the housing 110 to the bars 50 may utilise one or more supports 140. This attachment may be performed as a preliminary production step to form a sensing sub-unit that can then be provided for embedding into concrete. Pre-wiring and testing of this sensing sub-unit allows a reduction in time on the casting production line.

At operation 715, the rebars 50, along with the housing 110 and external sensors 150B, are now fixed into a segment (slab) mould for the concrete casting. The sub-unit produced in operation 710 may be transported to a concrete casting factory for operation 715. The sub-unit is attached to the casting mould in a straightforward manner, for example by two bolts 60 at each end of the rebars 50. It will be appreciated therefore that the inclusion of the sensing apparatus 100 within a slab 10 does not require complex features in the mould (for example, just two screw-holes at each end), and if needed these can be readily retro-fitted to existing moulds.

At operation 720, the segment mould is poured with concrete to cast slab 10, including the sensor assembly embedded therein. Typically the casting of a curved tunnel segment for example is performed with the concrete segment facing down, i.e. with the intrados underneath. The casting of a flag segment or slab segment would be different. The slab 10 is then installed at operation 725 into the tunnel lining (or other appropriate structure) and the sensor assemblies are activated at operation 730 and the network of nodes self-configures as described above.

As is known in the art, forming the slab may involve a concrete curing process, including pouring the concrete into the segment mould and subsequently vibrating the concrete, before baking the slab and then leaving the segment exposed to air for a more prolonged period, e.g. one month. In many cases, this curing is performed at a manufacturing site, and the cured slab is then transported to the desired installation site. It will be appreciated that the procedure of FIG. 8 (and variants thereof, such as discussed below), can be readily accommodated within an existing procedure with relatively little modification or disruption.

Note that the sequence of operations shown in FIG. 8 is provided by way of example only, and many variations will be apparent to the skilled person. For example, during the casting and curing (and possibly installation) of the concrete slab, a dummy lid (i.e. without internal electronics components 370) may be attached to the body of the housing 110 to prevent the ingress of concrete and any other contaminants into the enclosure 110. The dummy lid is then removed as part of operation 730 and the operational components then installed (rather than this being done at the start, at operation 705, as shown in FIG. 8). This approach avoids the risk of any damage to the internal components 370 during the casting of the slab, the installation of the slab 10 to a tunnel lining (or such-like), as well as during transportation of the slab to the site of installation. Conversely, in some cases, the internal components 370 may be inserted into the sensor assembly 100 at some intermediate point in the procedure, e.g. after the attachment of the housing 110 to the rebars 50 at operation 710, or after attachment of the housing to the segment mould at operation 715. In addition, the timing of attaching the external sensors 150B to the rebars may occur before, after, or at the same time as the housing 110 is attached to the rebars 50, providing the external sensors 150 are installed and wired to the enclosure 110 (and the interfacing PCB 330 therein) prior to casting the slab 10 at operation 720. Another potential variation is that the rebars are initially mounted into the slab mould, prior to attaching the external sensors 150B and/or the enclosure 110. Further variations will be apparent to the skilled person.

Figure 9:
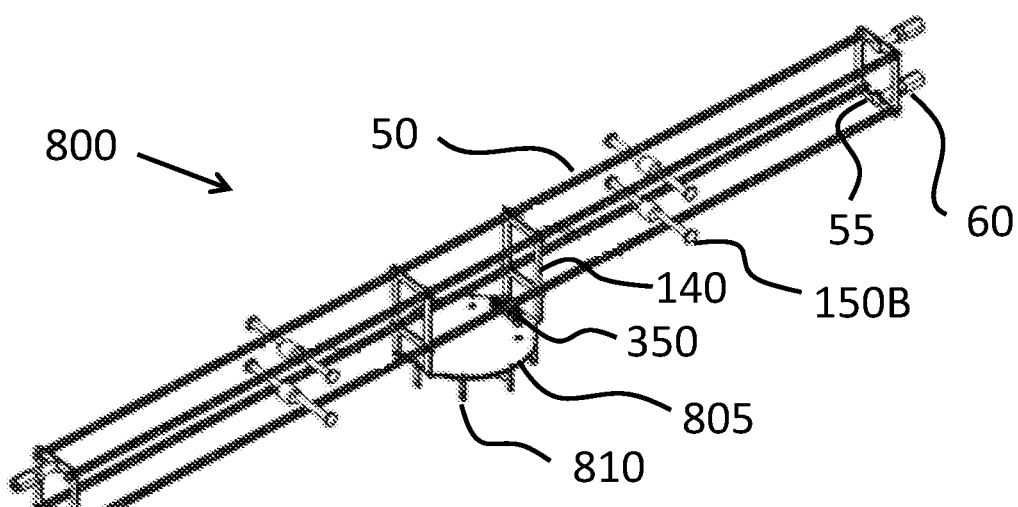
FIG. 9 is a further schematic diagram of one example of a sub assembly of a sensing apparatus.

FIG. 9 shows another embodiment of a sub-unit 800 forming a portion of a sensor assembly 100 which may be embedded within a segment 10 of a railway tunnel, such as shown in FIG. 1. The sub-unit 800 comprises a housing base plate 805 (i.e. for an enclosure) connected to a bracket 140 and one or more bars (or other appropriate structure(s)) 50 which are used to locate and retain a sensor assembly 100 within the concrete slab 10 (and also to reinforce the concrete slab). Various components of FIG. 9 have been discussed in detail in relation to, at least, FIGS. 2, 3, 5 and 6. However the example embodiment shown in FIG. 9 differs from the first example embodiment in that the housing or enclosure 110 is formed from a base plate on which is mounted a terminal module and a lid on which a control module, a wireless module and a battery are mounted but the side walls of the enclosure are formed from concrete of a concrete slab in which the sensor assembly 100 is embedded. For this example embodiment, a casting negative is used to form a void in the concrete which forms the enclosure 110.

FIG. 9 shows the bracket 140 comprises two opposing support portions that extend from the base plate 805 and engage the four reinforcing bars 50. In particular, each of the opposing support portions is provided with four holes or slots to receive and retain a corresponding rebar 50. It will be appreciated that bracket 140 represents just one example of a suitable mounting device, and other fixtures or methods for mounting the base plate 805 to the bars 50 will be apparent. Preferably, the base plate 805 and bracket 140 may be formed as a single unit (e.g. formed from a single metal piece) which is cut and bent/moulded to a desired shape. In other configurations the base plate 805 is mounted on to a top portion of the bracket 140 (separating the opposing support portions) by any suitable fixing, e.g. bolting or welding. The rebars 50 are held in the required configuration by support brackets 55; one bracket being located at each end of the bars 50. The support brackets 55 may be retained in a concrete mould using the mounting bolts 60.

The base plate 805 shown in FIG. 9 has a circular surface. The base plate 805 forms one face (i.e. the innermost face) of a cylindrical enclosure 110 of a sensor assembly 100. As such, the base plate 805 typically has a shape determined by the intended shape of the enclosure 110 of the sensor assembly 100. For example, if the enclosure 110 is intended to be cylindrical then the base plate 805 is circular, and if the enclosure 110 is intended to be a cube, the base plate 805 is square.

The base plate 805 may include a terminal module in the form of a PCB 330 (not shown) for connecting electronic components 370 within the enclosure 110 to any external sensors 150 (if present). As described above, the PCB 330 includes a first terminal module 360 for providing connections to any external sensors 150, which is electrically connected to a second terminal module 365 for providing connection to the internal components 370. The base plate 805 includes one or more gland holes 350 to allow wiring between the external sensors 150 and the first terminal module 360. It will be appreciated that implementations of sensor assemblies which do not include external sensors 150 may also not include gland holes or a PCB 330.

In contrast to the implementations of FIGS. 2 and 3, the implementation of FIG. 9 does not necessarily require a side wall extending around the circumference of the cylindrical shape. Instead, the base plate 805 may be temporarily attached to a casting negative which forms a cavity during the casting process. Said casting negative may be attached to the base plate 805 by one or more protrusions 810 which interact with corresponding features of the casting negative. In other examples, other methods of retaining the base plate against the casting negative may be used (i.e. clips and the like).

Figure 10:
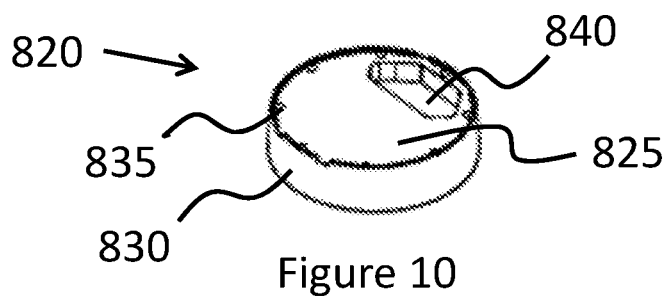
FIG. 10 is a schematic diagram of a casting negative for use in the installation of a sensor apparatus.

FIG. 10 shows an implementation of a casting negative 820 which may be used during the installation of a sensor assembly 100; for example with the sub-unit 800 of FIG. 9. The casting negative 820 is formed by a block or blank which defines a volume. The shape of the casting negative 820 corresponds substantially to the desired shape of the sensor assembly enclosure 110, such that it can be used to form an enclosure negative during the casting of a concrete slab 10. In other words, the presence of the casting negative creates a region around which the concrete solidifies (i.e. cures) which therefore forms a void or cavity for the enclosure 110 in the concrete cast 10 when the casting negative 820 is removed.

The casting negative 820 may have a base portion 825, having a size and shape corresponding to the base plate 805 of the sub-unit, and a circumferential wall 830, having a shape dependent on the shape of the base portion 825 (i.e. circular, square, hexagonal) and the required depth of enclosure in the slab 10. The casting negative 820 is removably detachable with the base plate 805. For example, the casting negative 820 may have a number of holes 835 for receiving a respective number of protrusions 810 of the base portion 825. The protrusions 810 providing a frictional hold on the casting negative 820. In general, the holes (and corresponding protrusions 810) are dispersed evenly and/or arranged symmetrically on the base portion 825.

In an alternative embodiment, the enclosure is formed using a casting negative which includes protrusions which extend from the casting negative to the base portion to form the enclosure. That is to say that in the alternative embodiment, the protrusions form part of the casting negative rather than being formed on the base plate. The effect however is the same in that the sensing apparatus is embedded in the concrete with the concreter forming side-walls of the enclosure in which the sensing apparatus is embedded.

The casting negative 820 may be formed from a single solid piece. For example, the casting negative 820 may be formed from a rubber material. The casting negative 820 should be made of materials which can stand the vibration during pouring and temperatures during initial cure. In some examples, the casting negative 820 may be reusable whilst in other examples the casting negative 820 may be single-use. It will be appreciated that the quality of the materials used for the casting negative 820 may be dependent on how reusable it is. In some examples, the casting negative 820 may be machined or 3D printed; however, it will be appreciated that other methods may be used. In some examples the casting negative 820 may be hollow or have an annular shape rather than being a solid volume.

The casting negative 820 may include a cavity 840 for providing an enclosure around the PCB (terminal module) 330 situated on the base plate. The cavity 840 will be inset from the circumferential wall 830 such that concrete is not able to infiltrate into the cavity 840 during the casting process. Such a cavity 840 may act to protect the sensor terminals during casting. It will be appreciated that casting negatives 820 may not include a cavity 840 if it is intended to be used with a base plate 805 which does not have a PCB 330.

Figure 11:
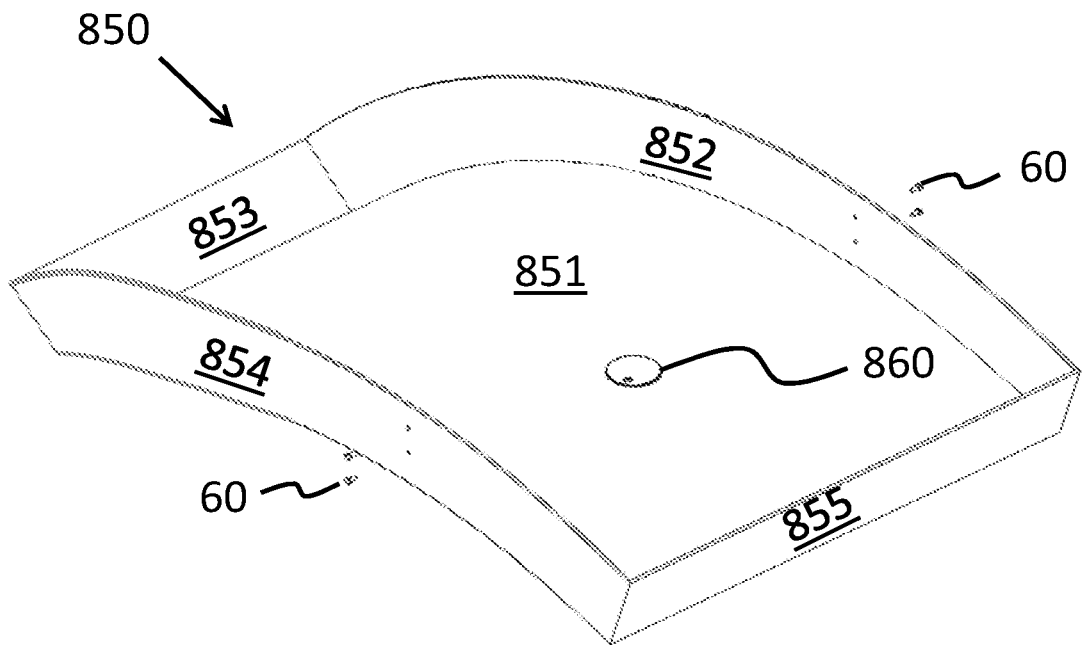
FIG. 11 is a schematic diagram of a mould for casting a concrete segment for use in the installations of a sensor apparatus.

FIG. 11 shows an implementation of a slab mould 850 which may be used during the installation of a sensor assembly 100; for example with the sub-unit 800 of FIG. 9 and the casting negative 820 of FIG. 10. The slab mould 850 defines a volume of a desired concrete slab. For example, a concrete slab 10 for use in a tunnel may have two parallel curved faces (i.e. an inner face and an outer face of the tunnel) and a plurality of side faces defining the limits of the two parallel curved faces.

The example slab mould 850 of FIG. 11 comprises an intrados wall 851 (i.e. Inner wall face) and four side walls 852,853,854,855. Two of the opposing side walls 852, 854 may include holes for receiving mounting bolts 60, used to retain a sub-unit 800 in place during casting. The intrados wall 851 includes an impression 860 which may be aligned to a casting negative 820, such that the impression 860 can be used to locate the casting negative 820. The impression 860 may be keyed to the casting negative 820 to ensure correct positioning. The impression 860 also acts (in addition to the mounting bolts 60) to prevent lateral movement of the casting negative 820 and sub-unit 800 during pouring of the concrete. The impression 860 may comprise a permanent low-profile modification to the mould's 850 intrados face 85. The impression 860 may be low profile to minimise the impact of the impression 860 when casting non-instrumented segments. For example, the impression 860 may be formed by creating an inset in the mould 850 only a few millimetres deep. The inset may have a shape corresponding to the exposed face of the casting negative 820, and hence a face of the desired sensor assembly 100 enclosure. The shape of the impression 860 allows the casting negative 820 to slot in (i.e. keying or fitting). Additionally, by slotting the casting negative 820 into the impression 860, the casting negative is slightly proud of the intrados face of the concrete slab 10 after the casting process is complete and the mould is removed. It will be appreciated that for moulds which are only to be used for casting instrumented segments, the impression 860 does not need to be low profile and instead could be several centimetres deep. This is known as a so called keying approach where the casting negative has a raised feature, but in other examples the casting negative may have a recessed feature and the segment mould may have a raised feature.

Figure 12:
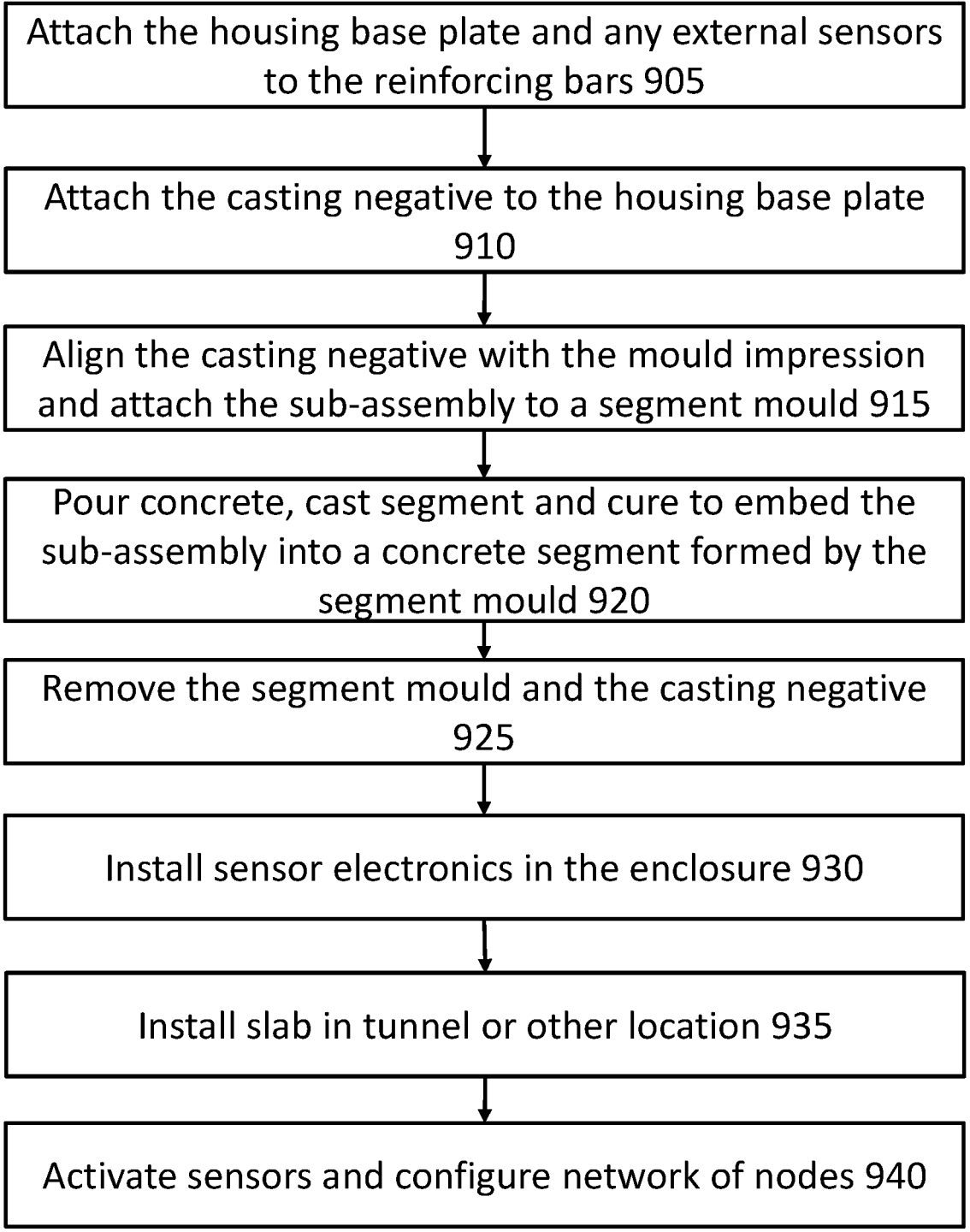
FIG. 12 is a flow diagram of a further example method for forming and installing the sensor assembly as described herein.

FIG. 12 is a flow diagram showing a further example of a method for installation of a sensor assembly 100 such as described herein. Initially at operation 905, the base plate 805 and the external sensors 150 (if any) are attached to the reinforcing bars (rebars) 50. Any external sensors 150B are wired up to the first terminal module 360 of the PCB 330 situated on the base plate 805 through the gland holes 350. As described above, the attachment of the base plate 805 to the bars 50 may utilise one or more supports 140. This attachment may be performed as a preliminary production step to form a sub-unit (sub-assembly) 800 that can then be provided for embedding into concrete. Pre-wiring and testing of this sub-unit allows a reduction in time on the casting production line. Said testing may include temporarily attaching internal components 370 of a sensor assembly 100; the internal components 370 then being removed prior to the next step of the operation.

At operation 910, a casting negative 820 may be attached to the base plate 805. For example by inserting protrusions 810 of the base plate 805 into corresponding holes 840 of the casting negative 820 to create a frictional hold. Operation 910 may be carried out before or after the sub-unit produced in operation 905 is transported to a concrete casting factory. As an alternative, the casting negative could be attached to the mould first, then the assembly 800 can be dropped into the mould.

At operation 915, the casting negative 820 is aligned with an impression 860 such that the casting negative 820 slots into the impression 860. The sub unit 800 including the casting negative 820 may be fixed into the segment (slab) mould for the concrete casting. The sub-unit is attached to the casting mould in a straightforward manner, for example by two bolts 60 at each end of the rebars 50. It will be appreciated therefore that the inclusion of the sensing apparatus 100 within a slab 10 does not require complex features in the mould (for example, just two screw-holes at each end), and if needed these can be readily retro-fitted to existing moulds. In some example the holes in the mould walls may be plugged for non-instrumental segment casting. In some examples, the attachment of the bolts 60 may occur alongside alignment of the impression, while in other examples it may occur subsequently.

At operation 920, the segment mould is poured with concrete to cast slab 10, including the sensor assembly embedded therein. Typically the casting is performed with the concrete segment facing down, i.e. with the intrados face underneath. During installation into the concrete slab 10, the casting negative defines a shape with a central axis aligned (parallel to) to radial axis of the tunnel, which has a top face that is generally parallel to the inner face of the concrete slab. As a result, the sub-unit 800 is embedded within the concrete segment 10 such that the casting negative remains exposed and accessible, but does not protrude into the tunnel.

At operation 925, after the casting process is complete, the mould 850 and the casting negative 820 can be removed. When the casting negative 820 is removed, it leaves behind a enclosure 110 for receiving components of a sensor assembly 100; the base of which is provided by the base plate 805 and the circumferential walls of which are provided by the concrete formerly in contact with the casting negative 820. A lid 130 may be provided to seal the enclosure 110.

At operation 930, the internal components 370 of the sensor assembly 100 can be installed into the cavity formed by removing the casting negative 820. During installation the internal components 370 can be wired into the second terminal module 365, if required. In some examples, the internal components 370 may be attached to a lid 130 of the enclosure 110. In these examples, installation may involve attaching the lid to the base plate 805 or to the concrete. A sealed enclosure is formed for the internal components 370 of the sensor assembly 100 between the base plate 805, concrete circumferential walls 830 and the lid 130. In some examples, the enclosure 110 may be further sealed by providing an additional boundary layer to the concrete circumferential walls 830. For example, a side wall may be inserted into the cavity defined by the concrete circumferential walls 830. The enclosure 110 may then be formed between this side wall, the base plate 805 and the lid 130. Alternatively, a coating may be applied to the concrete during the installation process.

As is known in the art, forming the slab may involve a concrete curing process, including pouring the concrete into the segment mould and subsequently vibrating the concrete, before baking the slab and then leaving the segment exposed to air for a more prolonged period, e.g. one month. In many cases, this curing is performed at a manufacturing site, and the cured slab is then transported to the desired installation site. It will be appreciated that the procedure of FIG. 12 (and variants thereof, such as discussed below), can be readily accommodated within an existing procedure with relatively little modification or disruption.

For example, the internal components 370 and lid 130 could be installed before the outdoor curing. Alternatively, in some examples the internal components could be installed after the outdoor curing. In these examples, the cavity may be covered by a temporary (self-adhesive) cover or lid which can be removed and discarded at a time of electronics installation, the lid or cover acting to prevent damage to the sensor connections. At operation 935, the slab 10 is then installed into the tunnel lining (or other appropriate structure), typically by using a vacuum erection process. The sensor assemblies are activated at operation 940 and the network of nodes self-configures as described above. According to example embodiments of the present technique therefore, the sensors can be activated before the segment is placed so that readings can be taken as the ring is built and the soil load comes onto the tunnel.

With regard to the methods of FIG. 8 and FIG. 12, there are various ways in which the sensor assembly might be activated. For example, if the internal components are not inserted into the enclosure 110 until after on-site installation, then they may be directly activated at this point, for example, by manually setting a switch or by adding the battery to the other internal components (so that the latter are powered on). Other possibilities include using some wireless device to activate the sensing assembly, for example using near field communications (NFC).

Once the sensor assembly 100 has been installed as shown in FIG. 8, it can be used to monitor environment conditions according to the types of sensors provided as part of the sensor assembly. As discussed above, such sensors 150 may include a tilt sensor for detecting a change in orientation of the housing and/or a strain sensor for detecting strain (in effect distortions of the concrete within the slab). Other sensors could be provided for various types of monitoring, including parameters such as temperature, moisture level, vibration, etc. More generally, the sensor assembly 100 can be readily modified, for example, to be used with different size rebars, to change the number and/or design of the sensors 150 provided, etc.

In a typical environment, multiple slabs 10 will be equipped with sensor assemblies, having regard to (i) sensing requirements and (ii) communication requirements. In other words, the distribution of sensor assemblies within the tunnel (or other environment), in terms of both azimuthal and longitudinal location, should provide useful monitoring data for understanding the state of the tunnel, and also provide a suitable number and configuration of nodes to form a robust wireless network.

Note that the number and type of sensors provided in a sensing apparatus 100 can vary according the requirements of any given installation. Furthermore, a given installation may use a mix of sensor assemblies, some provided with some forms of sensor, and other provided with other forms of sensor (or different combinations of sensors). In some circumstances it may be appropriate to embed multiple sensor assemblies within a single concrete slab (side or section). Although the sensor assemblies described herein have primarily been deployed in an underground tunnel, they could be deployed instead in a wide variety of other structures, including: overground (non-metro) train tunnel; car tunnel; bridge; office building; railway embankment, a sheet pile wall, and so on.

The sensor(s) can be used to monitor one or more environmental conditions for the concrete, for example, physical parameter(s) pertaining to or experienced by the concrete. As an example, a sensor may measure a physical parameter such as temperature, humidity, and/or chemical concentration within, or in the vicinity of, the concrete. Similarly, a sensor may measure vibrations within or experienced by the concrete; likewise, movement, tilt, stress, strain and/or distortion of the concrete may also be measured as physical parameters of interest. These measurements for monitoring environmental conditions may be performed directly on the concrete or indirectly. As an example of the latter approach, the vibration and/or tilt of the sensor apparatus 100 itself may first be measured or sensed, thereby allowing the vibration and/or tilt of the concrete to be inferred given the coupling of the sensor apparatus 100 to the concrete. It will be appreciated that these are just examples of how the sensors may be used to monitor environmental conditions for the concrete, and further approaches and physical parameters for monitoring will be apparent to the skilled person.

In conclusion, various embodiments of the invention have been described. The skilled person will appreciate that these embodiments are provided only by way of example, and different features from different embodiments can be combined as appropriate. Furthermore, the details of a sensor device will depend upon the particular environment in which it is installed, and the intended usage. Accordingly, the scope of the presently claimed invention is to be defined by the appended claims and their equivalents.

Further example aspects and features are defined in the following numbered paragraphs:

Paragraph 1. A battery-powered sensing apparatus adapted for embedding in concrete, the sensing apparatus comprising:
   a housing having a base portion and a removable lid, the enclosure providing a sealed enclosure;
   at least one sensor for monitoring one or more environmental conditions for the concrete;
   a control module;
   a wireless communication module; and
   a battery;
   wherein the control module, wireless communication module and battery are mounted on the lid so as to be located within the sealed enclosure as internal components, and so as to be removable with the lid after the sensing apparatus has been embedded in the concrete.

Paragraph 2. The sensing apparatus of paragraph 1, wherein the at least one sensor includes a sensor located within the sealed enclosure and mounted on the lid.

Paragraph 3. The sensing apparatus of paragraph 2, wherein the sensor located within the sealed enclosure comprises a tilt meter.

Paragraph 4. The sensing apparatus of any preceding paragraph, wherein the at least one sensor includes a sensor to be located externally to the sealed enclosure, embedded within the concrete, and the sensing apparatus further comprises a wired link from the externally located sensor into the sealed enclosure.

Paragraph 5. The sensing apparatus of paragraph 4, further comprising a dumb terminal module located in the base portion of the housing, said dumb terminal module providing an interface between said wired link from the externally located sensor and wiring from the internal components within the sealed enclosure.

Paragraph 6. The sensing apparatus of paragraph 5, wherein the wiring from the internal components can be plugged into and unplugged from the connector.

Paragraph 7. The sensing apparatus of any of paragraphs 4 to 6, wherein the externally located sensor comprises a vibrating wire strain gauge.

Paragraph 8. The sensing apparatus of any preceding paragraph, wherein the control module comprises a microcontroller responsible for controlling data sampling and timekeeping within the sensing apparatus.

Paragraph 9. The sensing apparatus of any preceding paragraph, wherein the wireless communication module is adapted to form a node in a wireless mesh network.

Paragraph 10. The sensing apparatus of paragraph 9, wherein the wireless communication module supports self-configuration of the wireless mesh network.

Paragraph 11. The sensing apparatus of paragraph 9 or 10, wherein the wireless communication module is configured to go into a low-power mode between pre-scheduled communication sessions with other nodes in the wireless mesh network.

Paragraph 12. The sensing apparatus of paragraph 11, wherein the wireless communication module is configured to communicate with other nodes in the wireless network according to a time-synchronised schedule such that transmit and receive circuits of the wireless communication system are in operation with an average duty cycle of less than 5%, preferably less than 1%.

Paragraph 13. The sensing apparatus of any preceding paragraph, wherein the sensing apparatus supports an operational lifetime of at least 10 years after embedding into the concrete.

Paragraph 14. The sensing apparatus of any preceding paragraph, wherein the battery has a charge capacity of at least 10 Ampere hours.

Paragraph 15. The sensing apparatus of any preceding paragraph, further comprising a gasket located between the lid and the base portion of the housing.

Paragraph 16. A sensing sub-unit comprising:
   the sensing apparatus of any preceding paragraph; and
   a structure for embedding within the concrete to provide reinforcement of the concrete;
   wherein the sensing apparatus is mounted to the reinforcing structure.

Paragraph 17. The sensing sub-unit of paragraph 16, wherein the reinforcing structure comprises multiple rebars.

Paragraph 18. A concrete slab including the sensing sub-unit of paragraph 16 or 17, wherein the lid of the sensing apparatus is substantially flush with the surface of the concrete slab.

Paragraph 19. The concrete slab of paragraph 18, wherein the concrete slab is curved to form part of a tunnel lining, wherein the lid of the sensing apparatus is located on the intrados surface of the concrete slab.

Paragraph 20. A battery-powered sensing apparatus adapted for embedding in concrete, the sensing apparatus comprising:
   a housing having a base portion and a removable lid, the housing providing a sealed enclosure;
   at least one sensor for monitoring one or more environmental conditions for the concrete;
   a control module;
   a wireless communication module; and
   a battery;
   wherein the sensing apparatus is adapted to have an operation lifetime of at least 10 years after the sensing apparatus has been embedded in the concrete.

Paragraph 21. The sensing apparatus of paragraph 20, wherein:
   the battery has a charge capacity of at least 10 Ampere hours;
   the control module comprises a microcontroller having a sleep mode drawing less than 0.01 milliamps; and
   the wireless communication module has a duty cycle of less than 5% and draws less than 0.01 milliamps when inactive.

Paragraph 22. A method for forming a concrete slab with an embedded sensing apparatus, the method comprising:
constructing a sub-unit comprising a sealed enclosure and a reinforcing structure;
attaching the sub-unit to a slab mould via the reinforcing structure; and
casting the concrete into the slab mould to embed the sub unit into a concrete slab;
wherein components of the sensing apparatus are included within sealed enclosure.

Paragraph 23. The method of paragraph 22, wherein the components of the sensing apparatus are included within the sealed enclosure after casting the concrete.

Paragraph 24. The method of paragraph 22 or 23, wherein the reinforcing structure comprises a plurality of rebars.

Paragraph 25. The method of any of paragraphs 22 to 24, wherein the sensing apparatus comprises the sensing apparatus of any of paragraphs 1-15, 20 or 21.

The invention claimed is:

1. A battery-powered sensing apparatus adapted for embedding in concrete, the sensing apparatus comprising:
    an enclosure having a base portion and a removable lid, the enclosure providing a sealed cavity;
    at least one sensor for monitoring one or more environmental conditions of the concrete by measuring at least one physical parameter of the concrete, wherein the at least one sensor includes a sensor located within the sealed enclosure and mounted on the lid;
    a control module;
    a wireless communication module; and
    a battery;
    wherein the control module, wireless communication module and battery are mounted on the lid so as to be located within the sealed enclosure as internal components, and so as to be removable with the lid after the sensing apparatus has been embedded in the concrete.

2. The sensing apparatus of claim 1, wherein the enclosure includes side-walls formed with the removable lid and the base portion to form a cavity within a housing when the sensing apparatus has been embedded in the concrete.

3. The sensing apparatus of claim 1, wherein the enclosure includes protrusions which extend from the base portion for receiving a casting negative to form, when the sensing apparatus is embedded in the concrete, side-walls of the enclosure being formed from the concrete in which the sensing apparatus is embedded.

4. The sensing apparatus of claim 1, wherein the enclosure is formed using a casting negative which includes protrusions which extend from the casting negative to the base portion to form the enclosure, when the sensing apparatus is embedded in the concrete, side-walls of the enclosure being formed from the concrete in which the sensing apparatus is embedded.

5. The sensing apparatus of claim 1, wherein the sensor located within the sealed enclosure comprises a tilt meter.

6. The sensing apparatus of claim 1, wherein the at least one sensor includes a sensor to be located externally to the sealed enclosure, embedded within the concrete, and the sensing apparatus further comprises a wired link from the externally located sensor into the sealed enclosure.

7. The sensing apparatus of claim 6, further comprising a terminal module located in the base portion of the sealed enclosure, said terminal module providing an interface between said wired link from the externally located sensor and wiring from the internal components within the sealed enclosure.

8. The sensing apparatus of claim 7, wherein the wiring from the internal components can be plugged into and unplugged from the terminal module.

9. The sensing apparatus of claim 6, wherein the externally located sensor comprises a vibrating wire strain gauge.

10. The sensing apparatus of claim 1, wherein the control module comprises a microcontroller responsible for controlling data sampling and timekeeping within the sensing apparatus.

11. The sensing apparatus of claim 1, wherein the wireless communication module is adapted to form a node in a wireless mesh network or geographical wide area network.

12. The sensing apparatus of claim 11, wherein the wireless communication module supports self-configuration of the wireless mesh network or the geographical wide area network.

13. The sensing apparatus of claim 11, wherein the wireless communication module is configured to go into a low-power mode between pre-scheduled communication sessions with other nodes in the wireless mesh network or the geographical wide area network.

14. The sensing apparatus of claim 13, wherein the wireless communication module is configured to communicate with other nodes in the wireless network according to a time-synchronised schedule such that transmit and receive circuits of the wireless communication system are in operation with an average duty cycle of less than 5%, preferably less than 1%.

15. The sensing apparatus of claim 13, wherein the wireless communication module is configured to communicate with other nodes in the geographical wide area network according to a non time-synchronised schedule with a low duty cycle/low power cycle.

16. A battery-powered sensing apparatus adapted for embedding in concrete, the sensing apparatus comprising:
    an enclosure having a base portion and a removable lid, the enclosure providing a sealed enclosure;
    at least one sensor for monitoring one or more environmental conditions of the concrete by measuring at least one physical parameter of the concrete, wherein the at least one sensor includes a sensor located within the sealed enclosure and mounted on the lid;
    a control module;
    a wireless communication module; and
    a battery;
    wherein the sensing apparatus is adapted to have an operation lifetime of at least 10 years after the sensing apparatus has been embedded in the concrete.

17. The sensing apparatus of claim 16, wherein:
    the battery has a charge capacity of at least 10 Ampere hours;
    the control module comprises a microcontroller having a sleep mode drawing less than 0.01 milliamps; and
    the wireless communication module has a duty cycle of less than 5% and draws less than 0.01 milliamps when in standby.

18. A method for forming a concrete slab with an embedded sensing apparatus, the method comprising:
    constructing a sub-unit comprising a sealed enclosure and a reinforcing structure; attaching the sub-unit to a slab mould via the reinforcing structure; and
    casting the concrete into the slab mould to embed the sub-unit into a concrete slab;
    wherein components of the sensing apparatus are included within the sealed enclosure, the sensing apparatus including at least one sensor for monitoring one or more environmental conditions of the concrete by measuring at least one physical parameter of the concrete, wherein the at least one sensor includes a sensor located within the sealed enclosure and mounted on a removable lid of the enclosure.

19. The method of claim 18, wherein the components of the sensing apparatus are included within the sealed enclosure after casting the concrete.

\* \* \* \* \*